US011724013B2

(12) United States Patent
Peterson et al.

(10) Patent No.: US 11,724,013 B2
(45) Date of Patent: *Aug. 15, 2023

(54) FLUID PURIFICATION SYSTEM

(71) Applicant: OUTSET MEDICAL, INC., San Jose, CA (US)

(72) Inventors: Richard B. Peterson, Corvallis, OR (US); James R. Curtis, Portland, OR (US)

(73) Assignee: Outset Medical, Inc., San Jose, CA (US)

( * ) Notice: Subject to any disclaimer, the term of this patent is extended or adjusted under 35 U.S.C. 154(b) by 121 days.

This patent is subject to a terminal disclaimer.

(21) Appl. No.: 17/028,130

(22) Filed: Sep. 22, 2020

(65) Prior Publication Data

US 2021/0069401 A1    Mar. 11, 2021

Related U.S. Application Data

(60) Division of application No. 16/138,441, filed on Sep. 21, 2018, now abandoned, which is a division of
(Continued)

(51) Int. Cl.
*A61M 1/16*    (2006.01)
*B01D 61/08*   (2006.01)
(Continued)

(52) U.S. Cl.
CPC ........ *A61M 1/1686* (2013.01); *A61M 1/1658* (2013.01); *A61M 1/1672* (2014.02);
(Continued)

(58) Field of Classification Search
CPC .............. A61M 1/1686; A61M 1/1658; A61M 1/1672; A61M 2205/75; B01D 61/025;
(Continued)

(56) References Cited

U.S. PATENT DOCUMENTS 1,662,870 A     3/1928   Stancliffe
3,356,360 A    12/1967   Ward
(Continued)

FOREIGN PATENT DOCUMENTS

CN    200951223 Y    9/2007
DE      8702995 U1   6/1987
(Continued)

OTHER PUBLICATIONS

Hu et al.; U.S. Appl. No. 17/607,637 entitled "Dialysis systems and methods," filed Oct. 29, 2021.
(Continued)

*Primary Examiner* — John Kim
(74) *Attorney, Agent, or Firm* — Shay Glenn LLP

(57) ABSTRACT

Certain disclosed embodiments concern systems and methods of preparing dialysate for use in a home dialysis system that is compact and light-weight relative to existing systems and consumes relatively low amounts of energy. The method includes coupling a household water stream to a dialysis system; filtering the water stream; heating the water stream to at least about 138 degrees Celsius in a non-batch process to produce a heated water stream; maintaining the heated water stream at or above at least about 138 degrees Celsius for at least about two seconds; cooling the heated water stream to produce a cooled water stream; ultrafiltering the cooled water stream; and mixing dialysate components into the cooled water stream in a non-batch process.

11 Claims, 14 Drawing Sheets

Related U.S. Application Data application No. 14/808,827, filed on Jul. 24, 2015, now Pat. No. 10,105,476, which is a continuation of application No. 13/965,720, filed on Aug. 13, 2013, now Pat. No. 9,138,687, which is a continuation of application No. 13/068,038, filed on Apr. 29, 2011, now Pat. No. 8,524,086, which is a continuation of application No. 12/795,382, filed on Jun. 7, 2010, now Pat. No. 8,501,009.

(51) Int. Cl.

| | | |
|---|---|---|
| *B01D 61/18* | (2006.01) | |
| *C02F 1/02* | (2023.01) | |
| *C02F 1/44* | (2023.01) | |
| *B01D 61/02* | (2006.01) | |
| *B01D 61/14* | (2006.01) | |
| *C02F 1/20* | (2023.01) | |
| *B01D 61/58* | (2006.01) | |
| *C02F 1/00* | (2023.01) | |
| *C02F 1/28* | (2023.01) | |
| *F24H 1/12* | (2022.01) | |
| *C02F 9/20* | (2023.01) | |
| *C02F 103/02* | (2006.01) | |

(52) U.S. Cl.
CPC ............ *B01D 61/08* (2013.01); *B01D 61/18* (2013.01); *B01D 61/58* (2013.01); *C02F 1/001* (2013.01); *C02F 1/02* (2013.01); *C02F 1/20* (2013.01); *C02F 1/283* (2013.01); *C02F 1/441* (2013.01); *C02F 1/444* (2013.01); *C02F 9/20* (2023.01); *F24H 1/121* (2013.01); *A61M 2205/75* (2013.01); *B01D 61/025* (2013.01); *B01D 61/145* (2013.01); *B01D 2311/04* (2013.01); *B01D 2311/06* (2013.01); *B01D 2311/25* (2013.01); *C02F 2103/026* (2013.01); *C02F 2209/005* (2013.01); *C02F 2209/006* (2013.01); *C02F 2209/03* (2013.01); *C02F 2301/043* (2013.01); *C02F 2301/046* (2013.01); *C02F 2303/04* (2013.01)

(58) Field of Classification Search
CPC ........ B01D 61/08; B01D 61/18; B01D 61/30; B01D 61/58; B01D 61/145; B01D 2311/04; B01D 2311/06; B01D 2311/25; C02F 1/001; C02F 1/02; C02F 1/20; C02F 1/283; C02F 1/441; C02F 1/444; C02F 9/005; C02F 2209/005; C02F 2209/006; C02F 2209/03; C02F 2301/043; C02F 2301/046; C02F 2103/026; C02F 2303/04; F24H 1/121
See application file for complete search history.

(56) References Cited

U.S. PATENT DOCUMENTS

| | | | |
|---|---|---|---|
| 3,695,445 A | 10/1972 | Esmond | |
| 3,710,237 A | 1/1973 | Watson et al. | |
| 3,762,032 A | 10/1973 | Bowling et al. | |
| 3,809,309 A | 5/1974 | Batista | |
| 3,827,563 A | 8/1974 | Boe et al. | |
| 3,965,008 A | 6/1976 | Dawson | |
| 4,080,295 A | 3/1978 | Riede | |
| 4,089,456 A | 5/1978 | Toppen et al. | |
| 4,100,068 A | 7/1978 | Jordan et al. | |
| 4,110,220 A | 8/1978 | Lavender | |
| 4,115,273 A | 9/1978 | Winstead | |
| 4,155,157 A | 5/1979 | Gersbacher | |
| 4,172,033 A | 10/1979 | Willock | |
| 4,194,014 A | 3/1980 | Hermans et al. | |
| 4,204,628 A | 5/1980 | Houston et al. | |
| 4,209,391 A | 6/1980 | Lipps | |
| 4,229,299 A | 10/1980 | Savitz et al. | |
| 4,231,366 A | 11/1980 | Schael | |
| 4,267,040 A | 5/1981 | Schal | |
| 4,293,409 A | 10/1981 | Riede et al. | |
| 4,310,416 A | 1/1982 | Tanaka et al. | |
| 4,317,725 A | 3/1982 | Kume et al. | |
| 4,342,651 A | 8/1982 | Ahrens | |
| 4,476,022 A | 10/1984 | Doll | |
| 4,486,303 A | 12/1984 | Brous | |
| 4,500,426 A | 2/1985 | Ishii et al. | |
| 4,508,622 A | 4/1985 | Polaschegg | |
| 4,536,201 A | 8/1985 | Brorsson et al. | |
| 4,560,472 A | 12/1985 | Granzow et al. | |
| 4,624,784 A | 11/1986 | Lefebvre | |
| 4,647,748 A | 3/1987 | Glassman | |
| 4,661,246 A | 4/1987 | Ash | |
| 4,689,108 A | 8/1987 | Barry, Jr. et al. | |
| 4,756,835 A | 7/1988 | Wilson | |
| 4,769,134 A | 9/1988 | Allan et al. | |
| 4,770,787 A | 9/1988 | Heath | |
| 4,773,991 A | 9/1988 | Aid | |
| 4,786,411 A | 11/1988 | Benattar et al. | |
| 4,827,430 A | 5/1989 | Aid | |
| 4,869,421 A | 9/1989 | Norris et al. | |
| 4,875,619 A | 10/1989 | Anderson et al. | |
| 4,889,635 A | 12/1989 | Chevallet | |
| 4,894,164 A | 1/1990 | Polaschegg | |
| 4,923,613 A | 5/1990 | Chevallet | |
| 5,087,930 A | 2/1992 | Roy et al. | |
| 5,092,836 A | 3/1992 | Polaschegg | |
| 5,094,749 A | 3/1992 | Seita et al. | |
| 5,147,605 A | 9/1992 | Tatsuno et al. | |
| 5,227,049 A | 7/1993 | Chevallet et al. | |
| 5,232,145 A | 8/1993 | Alley et al. | |
| 5,236,476 A | 8/1993 | Klick | |
| 5,247,434 A | 9/1993 | Peterson et al. | |
| 5,259,961 A | 11/1993 | Eigendorf | |
| 5,312,550 A | 5/1994 | Hester | |
| 5,313,023 A | 5/1994 | Johnson | |
| 5,316,676 A | 5/1994 | Drori | |
| 5,326,476 A | 7/1994 | Grogan et al. | |
| 5,334,392 A | 8/1994 | Senninger et al. | |
| 5,336,165 A | 8/1994 | Twardowski | |
| 5,342,326 A | 8/1994 | Peppel et al. | |
| 5,344,392 A | 9/1994 | Senninger et al. | |
| 5,346,472 A | 9/1994 | Keshaviah et al. | |
| 5,360,395 A | 11/1994 | Utterberg | |
| 5,385,623 A | 1/1995 | Diaz | |
| 5,394,732 A | 3/1995 | Johnson et al. | |
| 5,395,351 A | 3/1995 | Munsch | |
| 5,401,238 A | 3/1995 | Pirazzoli | |
| 5,409,612 A | 4/1995 | Maltais et al. | |
| 5,421,208 A | 6/1995 | Packard et al. | |
| 5,439,451 A | 8/1995 | Collinson et al. | |
| 5,469,264 A | 11/1995 | Shigemori | |
| 5,472,614 A | 12/1995 | Rossi | |
| 5,489,385 A | 2/1996 | Raabe et al. | |
| 5,498,253 A | 3/1996 | Aswad et al. | |
| 5,498,338 A | 3/1996 | Kruger et al. | |
| 5,503,624 A | 4/1996 | Roeher et al. | |
| 5,520,640 A | 5/1996 | Utterberg | |
| 5,526,357 A | 6/1996 | Jandrell | |
| 5,533,996 A | 7/1996 | Murphey et al. | |
| 5,534,328 A | 7/1996 | Ashmead et al. | |
| 5,536,258 A | 7/1996 | Folden | |
| 5,571,754 A | 11/1996 | Bertin et al. | |
| 5,580,460 A | 12/1996 | Polaschegg | |
| 5,580,523 A | 12/1996 | Bard | |
| 5,582,600 A | 12/1996 | Loh | |
| 5,591,016 A | 1/1997 | Kubota et al. | |
| 5,591,344 A | 1/1997 | Kenley et al. | |
| 5,593,581 A | 1/1997 | Lescoche | |
| 5,595,712 A | 1/1997 | Harbster et al. | |
| 5,609,770 A | 3/1997 | Zimmerman et al. | |
| 5,610,645 A | 3/1997 | Moore et al. | |
| 5,611,214 A | 3/1997 | Wegeng et al. | |
| 5,613,663 A | 3/1997 | Schmidt et al. | |

(56) References Cited

U.S. PATENT DOCUMENTS

| | | |
|---|---|---|
| 5,615,996 A | 4/1997 | Suzuki et al. |
| 5,618,268 A | 4/1997 | Raines et al. |
| 5,618,441 A | 4/1997 | Rosa et al. |
| 5,620,608 A | 4/1997 | Rosa et al. |
| 5,623,969 A | 4/1997 | Raines |
| 5,624,572 A | 4/1997 | Larson et al. |
| 5,629,871 A | 5/1997 | Love et al. |
| 5,630,804 A | 5/1997 | Imada et al. |
| 5,643,190 A | 7/1997 | Utterberg |
| 5,647,984 A | 7/1997 | Hovland et al. |
| 5,648,684 A | 7/1997 | Bertin et al. |
| 5,650,071 A | 7/1997 | Brugger et al. |
| 5,662,144 A | 9/1997 | Lo et al. |
| 5,685,835 A | 11/1997 | Brugger |
| 5,689,966 A | 11/1997 | Zess et al. |
| 5,693,008 A | 12/1997 | Brugger et al. |
| 5,698,916 A | 12/1997 | Eguchi |
| 5,711,883 A | 1/1998 | Folden et al. |
| 5,713,850 A | 2/1998 | Heilmann et al. |
| 5,725,773 A | 3/1998 | Polaschegg |
| 5,743,892 A | 4/1998 | Loh et al. |
| 5,744,031 A | 4/1998 | Bene |
| 5,749,226 A | 5/1998 | Bowman et al. |
| 5,796,985 A | 6/1998 | Kawakami et al. |
| 5,779,833 A | 7/1998 | Cawley et al. |
| 5,782,575 A | 7/1998 | Vincent et al. |
| 5,788,099 A | 8/1998 | Treu et al. |
| 5,788,851 A | 8/1998 | Kenley et al. |
| 5,792,367 A | 8/1998 | Mattisson et al. |
| 5,811,062 A | 9/1998 | Wegeng et al. |
| 5,813,235 A | 9/1998 | Peterson |
| 5,851,202 A | 12/1998 | Carlsson |
| 5,858,238 A | 1/1999 | Mcrea et al. |
| 5,858,239 A | 1/1999 | Kenley et al. |
| 5,861,555 A | 1/1999 | Hobro et al. |
| 5,868,930 A | 2/1999 | Kopf |
| 5,879,316 A | 3/1999 | Safar et al. |
| 5,881,774 A | 3/1999 | Utterberg |
| 5,885,456 A | 3/1999 | Charkoudian et al. |
| 5,895,368 A | 4/1999 | Utterberg |
| 5,903,211 A | 5/1999 | Flego et al. |
| 5,910,138 A | 6/1999 | Sperko et al. |
| 5,914,033 A | 6/1999 | Carlsson |
| 5,921,678 A | 7/1999 | Desai et al. |
| 5,928,177 A | 7/1999 | Brugger et al. |
| 5,928,180 A | 7/1999 | Krivitski et al. |
| 5,932,103 A | 8/1999 | Kenley et al. |
| 5,932,940 A | 8/1999 | Epstein et al. |
| 5,938,634 A | 8/1999 | Packard |
| 5,938,938 A | 8/1999 | Bosetto et al. |
| 5,951,863 A | 9/1999 | Kruger et al. |
| 5,951,870 A | 9/1999 | Utterberg |
| 5,957,898 A | 9/1999 | Jepson et al. |
| 5,974,867 A | 11/1999 | Forster et al. |
| 5,976,115 A | 11/1999 | Parris et al. |
| 5,983,947 A | 11/1999 | Utterberg |
| 5,984,903 A | 11/1999 | Nadal |
| 5,985,068 A | 11/1999 | Kawakami et al. |
| 5,993,174 A | 11/1999 | Konishi |
| 6,003,556 A | 12/1999 | Brugger et al. |
| 6,010,623 A | 1/2000 | Schnell et al. |
| 6,024,276 A | 2/2000 | Hirata et al. |
| 6,032,926 A | 3/2000 | Fuchs |
| 6,036,680 A | 3/2000 | Horne et al. |
| 6,039,877 A | 3/2000 | Chevallet et al. |
| 6,041,801 A | 3/2000 | Gray et al. |
| 6,044,691 A | 4/2000 | Kenley et al. |
| 6,048,432 A | 4/2000 | Ecer |
| 6,058,934 A | 5/2000 | Sullivan |
| 6,064,797 A | 5/2000 | Crittendon et al. |
| 6,066,261 A | 5/2000 | Spickermann |
| 6,071,269 A | 6/2000 | Schnell et al. |
| 6,074,559 A | 6/2000 | Hahmann et al. |
| 6,077,443 A | 6/2000 | Goldau |
| 6,082,891 A | 7/2000 | Schubert et al. |
| 6,100,463 A | 8/2000 | Ladd et al. |
| 6,109,994 A | 8/2000 | Cho et al. |
| 6,113,785 A | 9/2000 | Miura et al. |
| 6,117,115 A | 9/2000 | Hill et al. |
| 6,117,123 A | 9/2000 | Barney et al. |
| 6,121,539 A | 9/2000 | Johnson et al. |
| 6,123,798 A | 9/2000 | Gandhi et al. |
| 6,126,723 A | 10/2000 | Drost et al. |
| 6,126,831 A | 10/2000 | Goldau et al. |
| 6,129,973 A | 10/2000 | Martin et al. |
| 6,132,616 A | 10/2000 | Twardowski |
| 6,139,754 A | 10/2000 | Hartranft et al. |
| 6,142,008 A | 11/2000 | Cole et al. |
| 6,143,181 A | 11/2000 | Falkvall et al. |
| 6,143,247 A | 11/2000 | Sheppard et al. |
| 6,148,635 A | 11/2000 | Beebe et al. |
| 6,153,102 A | 11/2000 | Kenley et al. |
| 6,165,149 A | 12/2000 | Utterberg et al. |
| 6,165,161 A | 12/2000 | York et al. |
| 6,167,910 B1 | 1/2001 | Chow |
| 6,187,198 B1 | 2/2001 | Utterberg |
| 6,187,199 B1 | 2/2001 | Goldau |
| 6,192,596 B1 | 2/2001 | Bennett et al. |
| 6,193,462 B1 | 2/2001 | Kubota |
| 6,202,312 B1 | 3/2001 | Rando |
| 6,203,522 B1 | 3/2001 | Holmberg et al. |
| 6,203,535 B1 | 3/2001 | Barney et al. |
| 6,212,333 B1 | 4/2001 | Olk et al. |
| 6,220,299 B1 | 4/2001 | Arvidsson et al. |
| 6,221,040 B1 | 4/2001 | Kleinekofort |
| 6,221,064 B1 | 4/2001 | Nadal |
| 6,223,130 B1 | 4/2001 | Gray et al. |
| 6,225,497 B1 | 5/2001 | Becker et al. |
| 6,234,773 B1 | 5/2001 | Hill et al. |
| 6,251,279 B1 | 6/2001 | Peterson et al. |
| 6,254,567 B1 | 7/2001 | Treu et al. |
| 6,254,754 B1 | 7/2001 | Ross et al. |
| 6,258,276 B1 | 7/2001 | Mika et al. |
| 6,261,282 B1 | 7/2001 | Jepson et al. |
| 6,277,277 B1 | 8/2001 | Jacobi et al. |
| 6,280,406 B1 | 8/2001 | Dolecek et al. |
| 6,284,141 B1 | 9/2001 | Shaldon et al. |
| 6,302,653 B1 | 10/2001 | Bryant et al. |
| 6,308,721 B1 | 10/2001 | Bock et al. |
| 6,309,673 B1 | 10/2001 | Duponchelle et al. |
| 6,322,551 B1 | 11/2001 | Brugger |
| 6,323,662 B2 | 11/2001 | Ferri |
| 6,325,774 B1 | 12/2001 | Bene et al. |
| 6,329,139 B1 | 12/2001 | Nova et al. |
| 6,331,252 B1 | 12/2001 | El Sayyid et al. |
| 6,334,301 B1 | 1/2002 | Otsap et al. |
| 6,343,614 B1 | 2/2002 | Gray et al. |
| 6,344,033 B1 | 2/2002 | Jepson et al. |
| 6,346,084 B1 | 2/2002 | Schnell et al. |
| 6,347,711 B1 | 2/2002 | Goebel et al. |
| 6,349,170 B1 | 2/2002 | Fressinet et al. |
| 6,350,260 B1 | 2/2002 | Goebel et al. |
| 6,352,577 B1 | 3/2002 | Martin et al. |
| 6,355,161 B1 | 3/2002 | Shah et al. |
| 6,357,332 B1 | 3/2002 | Vecchio |
| 6,365,041 B1 | 4/2002 | Hoadley |
| 6,368,505 B1 | 4/2002 | Grummert et al. |
| 6,375,871 B1 | 4/2002 | Bentsen et al. |
| 6,382,923 B1 | 5/2002 | Gray |
| 6,387,069 B1 | 5/2002 | Utterberg |
| 6,395,180 B2 | 5/2002 | Chioini et al. |
| 6,415,860 B1 | 7/2002 | Kelly et al. |
| 6,416,293 B1 | 7/2002 | Bouchard et al. |
| 6,423,022 B1 | 7/2002 | Roeher et al. |
| 6,432,309 B1 | 8/2002 | Fuke et al. |
| 6,454,736 B1 | 9/2002 | Ludt et al. |
| 6,454,942 B1 | 9/2002 | Shintani et al. |
| 6,468,056 B1 | 10/2002 | Murakoshi |
| 6,477,058 B1 | 11/2002 | Leubs et al. |
| 6,481,982 B1 | 11/2002 | Yokomichi |
| 6,485,263 B1 | 11/2002 | Bryant et al. |
| 6,488,842 B2 | 12/2002 | Nagaoka |
| 6,488,872 B1 | 12/2002 | Beebe et al. |
| 6,490,812 B1 | 12/2002 | Bennett et al. |

(56) References Cited

U.S. PATENT DOCUMENTS

| | | |
|---|---|---|
| 6,503,062 B1 | 1/2003 | Gray et al. |
| 6,514,225 B1 | 2/2003 | Utterberg et al. |
| 6,514,412 B1 | 2/2003 | Insley et al. |
| 6,526,357 B1 | 2/2003 | Soussan et al. |
| 6,527,728 B2 | 3/2003 | Zhang |
| 6,530,262 B1 | 3/2003 | Esser |
| 6,533,840 B2 | 3/2003 | Martin et al. |
| 6,536,742 B2 | 3/2003 | Lotz et al. |
| 6,537,506 B1 | 3/2003 | Schwalbe et al. |
| 6,544,229 B1 | 4/2003 | Danby et al. |
| 6,546,998 B2 | 4/2003 | Oh et al. |
| 6,554,789 B1 | 4/2003 | Brugger et al. |
| 6,572,576 B2 | 6/2003 | Brugger et al. |
| 6,572,641 B2 | 6/2003 | Brugger et al. |
| 6,575,927 B1 | 6/2003 | Weitzel et al. |
| 6,579,241 B2 | 6/2003 | Roeher |
| 6,579,253 B1 | 6/2003 | Burbank et al. |
| 6,581,906 B1 | 6/2003 | Pott et al. |
| 6,582,385 B2 | 6/2003 | Burbank et al. |
| 6,592,558 B2 | 7/2003 | Quah |
| 6,601,432 B1 | 8/2003 | Ericson et al. |
| 6,602,424 B1 | 8/2003 | Krämer et al. |
| 6,604,908 B1 | 8/2003 | Bryant et al. |
| 6,607,644 B1 | 8/2003 | Apffel, Jr. |
| 6,607,697 B1 | 8/2003 | Müller |
| 6,616,877 B2 | 9/2003 | Close et al. |
| 6,616,909 B1 | 9/2003 | Tonkovich et al. |
| 6,623,860 B2 | 9/2003 | Hu et al. |
| 6,630,068 B1 | 10/2003 | Vinci |
| 6,635,226 B1 | 10/2003 | Tso et al. |
| 6,640,611 B2 | 11/2003 | Ericson et al. |
| 6,649,046 B2 | 11/2003 | Chevallet |
| 6,649,063 B2 | 11/2003 | Brugger et al. |
| 6,652,627 B1 | 11/2003 | Tonkovich et al. |
| 6,653,841 B1 | 11/2003 | Koerdt et al. |
| 6,654,660 B1 | 11/2003 | Singh et al. |
| 6,656,315 B2 | 12/2003 | Sallavanti et al. |
| 6,666,840 B1 | 12/2003 | Falkvall et al. |
| 6,666,909 B1 | 12/2003 | TeGrotenhuis et al. |
| 6,672,502 B1 | 1/2004 | Paul et al. |
| 6,673,311 B1 | 1/2004 | Sotoyama et al. |
| 6,676,621 B1 | 1/2004 | Menninger |
| 6,676,835 B2 | 1/2004 | O'Connor et al. |
| 6,684,710 B2 | 2/2004 | Chevallet et al. |
| 6,685,831 B2 | 2/2004 | Dönig et al. |
| 6,686,946 B2 | 2/2004 | Masuda et al. |
| 6,688,381 B2 | 2/2004 | Pence et al. |
| 6,695,807 B2 | 2/2004 | Bell et al. |
| 6,716,356 B2 | 4/2004 | Collins et al. |
| 6,730,233 B2 | 5/2004 | Pedrazzi |
| 6,731,216 B2 | 5/2004 | Ho et al. |
| 6,733,676 B2 | 5/2004 | Takai |
| 6,736,789 B1 | 5/2004 | Spickermann |
| 6,737,026 B1 | 5/2004 | Bergh et al. |
| 6,738,052 B1 | 5/2004 | Manke et al. |
| 6,743,193 B2 | 6/2004 | Brugger et al. |
| 6,744,038 B2 | 6/2004 | Wang et al. |
| 6,746,514 B2 | 6/2004 | Bedingfield et al. |
| 6,749,814 B1 | 6/2004 | Bergh et al. |
| 6,767,333 B1 | 7/2004 | Müller et al. |
| 6,775,577 B2 | 8/2004 | Cmkovich et al. |
| 6,793,831 B1 | 9/2004 | Paul et al. |
| 6,796,831 B1 | 9/2004 | Paul et al. |
| 6,797,056 B2 | 9/2004 | David |
| 6,804,991 B2 | 10/2004 | Balschat et al. |
| 6,806,947 B1 | 10/2004 | Ekdahl et al. |
| 6,811,707 B2 | 11/2004 | Rovatti et al. |
| 6,814,547 B2 | 11/2004 | Childers et al. |
| 6,814,726 B1 | 11/2004 | Lauer |
| 6,814,859 B2 | 11/2004 | Koehler et al. |
| 6,818,179 B1 | 11/2004 | Edgson et al. |
| 6,821,432 B2 | 11/2004 | Metzner |
| 6,827,698 B1 | 12/2004 | Kleinekofort |
| 6,830,693 B2 | 12/2004 | Govoni et al. |
| 6,838,156 B1 | 1/2005 | Neyer et al. |
| 6,852,231 B2 | 2/2005 | Ivansons et al. |
| 6,858,137 B2 | 2/2005 | Hahmann et al. |
| 6,863,867 B2 | 3/2005 | Bussche et al. |
| 6,868,309 B1 | 3/2005 | Begelman |
| 6,869,538 B2 | 3/2005 | Yu et al. |
| 6,871,838 B2 | 3/2005 | Raines et al. |
| 6,877,713 B1 | 4/2005 | Gray et al. |
| 6,878,283 B2 | 4/2005 | Thompson |
| 6,880,034 B2 | 4/2005 | Manke et al. |
| 6,881,344 B2 | 4/2005 | Vasta et al. |
| 6,889,556 B2 | 5/2005 | Steger |
| 6,892,781 B2 | 5/2005 | McHerron et al. |
| 6,903,332 B2 | 6/2005 | Weiss et al. |
| 6,905,479 B1 | 6/2005 | Bouchard et al. |
| 6,911,262 B2 | 6/2005 | Sallavanti et al. |
| 6,913,877 B1 | 7/2005 | Chaplen et al. |
| 6,929,751 B2 | 8/2005 | Bowman, Jr. et al. |
| 6,936,031 B2 | 8/2005 | Caleffi |
| 6,939,111 B2 | 9/2005 | Huitt et al. |
| 6,939,471 B2 | 9/2005 | Gross et al. |
| 6,952,963 B2 | 10/2005 | Delnevo |
| 6,953,323 B2 | 10/2005 | Childers et al. |
| 6,955,655 B2 | 10/2005 | Burbank et al. |
| 6,967,002 B1 | 11/2005 | Edgson et al. |
| 6,974,301 B2 | 12/2005 | Suzuki et al. |
| 6,976,964 B2 | 12/2005 | Chevallet et al. |
| 6,979,309 B2 | 12/2005 | Burbank et al. |
| 6,981,522 B2 | 1/2006 | O'Connor et al. |
| 6,986,428 B2 | 1/2006 | Hester et al. |
| 6,989,134 B2 | 1/2006 | Tonkovich et al. |
| 6,994,829 B2 | 2/2006 | Whyatt et al. |
| 7,004,924 B1 | 2/2006 | Brugger et al. |
| 7,014,705 B2 | 3/2006 | David |
| 7,021,148 B2 | 4/2006 | Kuhn et al. |
| 7,022,098 B2 | 4/2006 | Wariar et al. |
| 7,029,456 B2 | 4/2006 | Ware et al. |
| 7,033,498 B2 | 4/2006 | Wong |
| 7,033,539 B2 | 4/2006 | Krensky et al. |
| 7,040,142 B2 | 5/2006 | Burbank |
| 7,044,432 B2 | 5/2006 | Beden et al. |
| 7,044,927 B2 | 5/2006 | Mueller et al. |
| 7,063,512 B2 | 6/2006 | Haesloop et al. |
| 7,070,589 B2 | 7/2006 | Lolachi et al. |
| 7,074,191 B2 | 7/2006 | Bosetto et al. |
| 7,087,033 B2 | 8/2006 | Brugger et al. |
| 7,087,036 B2 | 8/2006 | Busby et al. |
| 7,094,345 B2 | 8/2006 | Gilbert et al. |
| 7,097,800 B2 | 8/2006 | Vigna et al. |
| 7,112,273 B2 | 9/2006 | Weigel et al. |
| 7,114,701 B2 | 10/2006 | Peppel |
| 7,115,206 B2 | 10/2006 | Chevallet et al. |
| 7,115,228 B2 | 10/2006 | Lundtveit et al. |
| 7,118,920 B2 | 10/2006 | Brophy et al. |
| 7,121,815 B2 | 10/2006 | Knuth et al. |
| 7,122,149 B2 | 10/2006 | Li et al. |
| 7,122,156 B2 | 10/2006 | Bergh et al. |
| 7,125,540 B1 | 10/2006 | Wegeng et al. |
| 7,131,956 B1 | 11/2006 | Pirazzoli et al. |
| 7,147,615 B2 | 12/2006 | Wariar et al. |
| 7,150,815 B2 | 12/2006 | Ashmead et al. |
| 7,152,469 B2 | 12/2006 | Milleker et al. |
| 7,163,531 B2 | 1/2007 | Seese et al. |
| 7,166,084 B2 | 1/2007 | Utterberg |
| 7,168,334 B1 | 1/2007 | Drott |
| 7,170,591 B2 | 1/2007 | Ohishi et al. |
| 7,175,697 B2 | 2/2007 | Neri |
| 7,186,342 B2 | 3/2007 | Pirazzoli et al. |
| 7,188,151 B2 | 3/2007 | Kumar et al. |
| 7,211,442 B2 | 5/2007 | Gilbert et al. |
| 7,214,312 B2 | 5/2007 | Brugger et al. |
| 7,217,108 B2 | 5/2007 | Herwig et al. |
| 7,217,364 B2 | 5/2007 | Lauer et al. |
| 7,223,262 B2 | 5/2007 | Brehm et al. |
| 7,223,338 B2 | 5/2007 | Duchamp et al. |
| 7,232,418 B2 | 6/2007 | Neri et al. |
| 7,238,164 B2 | 7/2007 | Childers et al. |
| 7,247,146 B2 | 7/2007 | Tonelli et al. |
| 7,264,723 B2 | 9/2007 | Sing et al. |
| 7,279,134 B2 | 10/2007 | Chan et al. |

(56) References Cited

U.S. PATENT DOCUMENTS

| | | | |
|---|---|---|---|
| 7,291,123 B2 | 11/2007 | Baraldi et al. | |
| 7,306,197 B2 | 12/2007 | Parrino et al. | |
| 7,314,061 B2 | 1/2008 | Peppel | |
| 7,316,780 B1 | 1/2008 | Fendya et al. | |
| 7,337,674 B2 | 3/2008 | Burbank et al. | |
| 7,341,568 B2 | 3/2008 | Zhang | |
| 7,354,426 B2 | 4/2008 | Young | |
| 7,355,685 B2 | 4/2008 | Scibona et al. | |
| 7,378,280 B2 | 5/2008 | Quake et al. | |
| 7,381,195 B2 | 6/2008 | Mori et al. | |
| 7,393,337 B2 | 7/2008 | Tonelli et al. | |
| 7,402,249 B2 | 7/2008 | Ikeda | |
| 7,469,716 B2 | 12/2008 | Parrino et al. | |
| 7,470,265 B2 | 12/2008 | Brugger et al. | |
| 7,488,301 B2 | 2/2009 | Beden et al. | |
| 7,488,447 B2 | 2/2009 | Sternby | |
| 7,493,824 B2 | 2/2009 | Brucksch et al. | |
| 7,494,590 B2 | 2/2009 | Felding et al. | |
| 7,501,101 B2 | 3/2009 | Wegeng et al. | |
| 7,503,908 B2 | 3/2009 | Bartholomew | |
| 7,507,380 B2 | 3/2009 | Chang et al. | |
| 7,510,545 B2 | 3/2009 | Peppel | |
| 7,517,332 B2 | 4/2009 | Tonelli et al. | |
| 7,517,387 B2 | 4/2009 | Chevallet et al. | |
| 7,520,919 B2 | 4/2009 | Caleffi | |
| 7,534,315 B1 | 5/2009 | Singh et al. | |
| 7,537,687 B2 | 5/2009 | Toyoda et al. | |
| 7,544,300 B2 | 6/2009 | Brugger et al. | |
| 7,551,043 B2 | 6/2009 | Nguyen et al. | |
| 7,559,911 B2 | 7/2009 | Giannella | |
| 7,575,562 B2 | 8/2009 | Oishi et al. | |
| 7,575,564 B2 | 8/2009 | Childers | |
| 7,591,449 B2 | 9/2009 | Raines et al. | |
| 7,603,907 B2 | 10/2009 | Reiter et al. | |
| 7,615,035 B2 | 11/2009 | Peppel | |
| 7,618,531 B2 | 11/2009 | Sugioka et al. | |
| 7,622,043 B2 | 11/2009 | Sawada et al. | |
| 7,632,470 B2 | 12/2009 | Tabata et al. | |
| 7,647,834 B2 | 1/2010 | O'Mahony et al. | |
| 7,648,474 B2 | 1/2010 | Paolini et al. | |
| 7,648,476 B2 | 1/2010 | Bock et al. | |
| 7,648,792 B2 | 1/2010 | Kaschmitter et al. | |
| 7,656,527 B2 | 2/2010 | Scarpaci | |
| 7,661,294 B2 | 2/2010 | Dam | |
| 7,671,974 B2 | 3/2010 | O'Mahony et al. | |
| 7,682,328 B2 | 3/2010 | Han et al. | |
| 7,686,778 B2 | 3/2010 | Burbank et al. | |
| 7,699,992 B2 | 4/2010 | Sternby | |
| 7,708,714 B2 | 5/2010 | Connell et al. | |
| 7,713,226 B2 | 5/2010 | Ash et al. | |
| 7,726,361 B2 | 6/2010 | Bartholomew | |
| 7,727,220 B2 | 6/2010 | Wieslander et al. | |
| 7,744,553 B2 | 6/2010 | Kelly et al. | |
| 7,749,184 B2 | 7/2010 | Cavalcanti et al. | |
| 7,758,082 B2 | 7/2010 | Weigel et al. | |
| 7,758,547 B2 | 7/2010 | Tonelli et al. | |
| 7,771,379 B2 | 8/2010 | Treu | |
| 7,771,380 B2 | 8/2010 | Jönsson et al. | |
| 7,775,986 B2 | 8/2010 | Roeher et al. | |
| 7,776,219 B2 | 8/2010 | Brugger et al. | |
| 7,780,848 B2 | 8/2010 | Kim et al. | |
| 7,788,038 B2 | 8/2010 | Oshita et al. | |
| 7,790,029 B2 | 9/2010 | Dannenmaier et al. | |
| 7,794,141 B2 | 9/2010 | Perry et al. | |
| 7,794,419 B2 | 9/2010 | Paolini et al. | |
| 7,801,746 B2 | 9/2010 | Moll et al. | |
| 7,815,852 B2 | 10/2010 | Sternby | |
| 7,824,354 B2 | 11/2010 | Vinci et al. | |
| 7,846,489 B2 | 12/2010 | Chang | |
| 7,871,390 B2 | 1/2011 | Rambod et al. | |
| 7,873,489 B2 | 1/2011 | Dolgos et al. | |
| 7,896,831 B2 | 3/2011 | Sternby et al. | |
| 7,901,579 B2 | 3/2011 | Brugger et al. | |
| 7,913,751 B2 | 3/2011 | Zwittig | |
| 7,918,993 B2 | 4/2011 | Harraway | |
| 7,922,899 B2 | 4/2011 | Vasta et al. | |
| 7,955,504 B1 | 6/2011 | Jovanovic et al. | |
| 7,968,250 B2 | 6/2011 | Kaschmitter | |
| 8,002,727 B2 | 8/2011 | Brugger et al. | |
| 8,012,114 B2 | 9/2011 | Daniel et al. | |
| 8,075,509 B2 | 12/2011 | Molducci et al. | |
| 8,105,265 B2 | 1/2012 | Demers et al. | |
| 8,105,266 B2 | 1/2012 | Childers et al. | |
| 8,137,554 B2 | 3/2012 | Jovanovic et al. | |
| 8,182,440 B2 | 5/2012 | Cruz et al. | |
| 8,182,691 B2 | 5/2012 | Stahl | |
| 8,190,651 B2 | 5/2012 | Treu et al. | |
| 8,192,387 B2 | 6/2012 | Brugger et al. | |
| 8,210,049 B2 | 7/2012 | Brugger | |
| 8,235,931 B2 | 8/2012 | Burbank et al. | |
| 8,236,599 B2 | 8/2012 | Chang et al. | |
| 8,267,881 B2 | 9/2012 | O'Mahony et al. | |
| 8,273,245 B2 | 9/2012 | Jovanovic et al. | |
| 8,293,113 B2 | 10/2012 | Jönsson et al. | |
| 8,293,114 B2 | 10/2012 | Jönsson et al. | |
| 8,298,427 B2 | 10/2012 | Ficheux et al. | |
| 8,323,492 B2 | 12/2012 | Childers et al. | |
| 8,329,030 B2 | 12/2012 | Childers et al. | |
| 8,343,085 B2 | 1/2013 | Toyoda et al. | |
| 8,394,046 B2 | 3/2013 | Nuernberger et al. | |
| 8,414,182 B2 | 4/2013 | Paul et al. | |
| 8,419,945 B2 | 4/2013 | Browning et al. | |
| 8,425,471 B2 | 4/2013 | Grant et al. | |
| 8,449,487 B2 | 5/2013 | Hovland et al. | |
| 8,460,228 B2 | 6/2013 | Burbank et al. | |
| 8,475,398 B2 | 7/2013 | O'Mahony | |
| 8,491,518 B2 | 7/2013 | Schnell et al. | |
| 8,496,824 B2 | 7/2013 | Remkes et al. | |
| 8,501,009 B2 * | 8/2013 | Peterson | A61M 1/1686 422/38 |
| 8,506,536 B2 | 8/2013 | Schnell | |
| 8,512,553 B2 | 8/2013 | Cicchello et al. | |
| 8,512,554 B2 | 8/2013 | Yu et al. | |
| 8,524,086 B2 * | 9/2013 | Peterson | C02F 1/441 210/134 |
| 8,529,491 B2 | 9/2013 | Beiriger | |
| 8,535,525 B2 | 9/2013 | Heyes et al. | |
| 8,603,020 B2 | 12/2013 | Roger et al. | |
| 8,608,658 B2 | 12/2013 | Burbank et al. | |
| 8,647,290 B2 | 2/2014 | Masala et al. | |
| 8,679,348 B2 | 3/2014 | Burbank et al. | |
| 8,685,244 B2 | 4/2014 | Heyes et al. | |
| 8,685,251 B2 * | 4/2014 | Smejtek | C02F 9/005 210/652 |
| 8,753,515 B2 | 6/2014 | Curtis et al. | |
| 8,801,922 B2 * | 8/2014 | Wrazel | A61M 1/14 210/205 |
| 8,840,581 B2 | 9/2014 | McGill et al. | |
| 9,024,746 B2 | 5/2015 | Burbank et al. | |
| 9,097,370 B2 | 8/2015 | Schnell et al. | |
| 9,138,687 B2 * | 9/2015 | Peterson | A61M 1/1672 |
| 9,220,828 B2 | 12/2015 | Coates | |
| 9,328,969 B2 | 5/2016 | Wrazel et al. | |
| 9,402,945 B2 | 8/2016 | Hogard et al. | |
| 9,480,455 B2 | 11/2016 | Buckberry | |
| 9,482,218 B2 | 11/2016 | Coates et al. | |
| 9,504,777 B2 | 11/2016 | Hogard et al. | |
| 9,545,469 B2 | 1/2017 | Curtis et al. | |
| 9,579,440 B2 | 2/2017 | Hogard et al. | |
| 9,592,029 B2 | 3/2017 | Buckberry | |
| 9,636,444 B2 | 5/2017 | Burbank et al. | |
| 9,700,663 B2 | 7/2017 | Burbank et al. | |
| 9,895,480 B2 * | 2/2018 | Wrazel | C02F 1/02 |
| 10,105,476 B2 * | 10/2018 | Peterson | C02F 1/444 |
| 10,668,201 B2 * | 6/2020 | Wrazel | A61M 1/1666 |
| 2002/0023879 A1 | 2/2002 | Hadden | |
| 2002/0032398 A1 | 3/2002 | Steele et al. | |
| 2002/0045265 A1 | 4/2002 | Bergh et al. | |
| 2002/0088751 A1 | 7/2002 | Rosenqvist et al. | |
| 2002/0108859 A1 | 8/2002 | Wang et al. | |
| 2002/0108869 A1 | 8/2002 | Savtchenko et al. | |
| 2002/0115200 A1 | 8/2002 | Zou et al. | |
| 2002/0162784 A1 | 11/2002 | Kohlheb et al. | |
| 2002/0187069 A1 | 12/2002 | Levin et al. | |

(56) References Cited

U.S. PATENT DOCUMENTS

| | | |
|---|---|---|
| 2003/0010717 A1 | 1/2003 | Brugger et al. |
| 2003/0039169 A1 | 2/2003 | Ehrfeld et al. |
| 2003/0052429 A1 | 3/2003 | Vigna et al. |
| 2003/0082066 A1 | 5/2003 | Hajaligol et al. |
| 2003/0138349 A1 | 7/2003 | Robinson et al. |
| 2003/0156991 A1 | 8/2003 | Halas et al. |
| 2003/0163077 A1 | 8/2003 | Kim et al. |
| 2003/0168590 A1 | 9/2003 | Weiss et al. |
| 2003/0183345 A1 | 10/2003 | Soberay |
| 2003/0220598 A1 | 11/2003 | Busby et al. |
| 2003/0221777 A1 | 12/2003 | McHerron et al. |
| 2004/0004589 A1 | 1/2004 | Shih |
| 2004/0008370 A1 | 1/2004 | Keane et al. |
| 2004/0012122 A1 | 1/2004 | Nagaoka et al. |
| 2004/0016700 A1 | 1/2004 | Kellam et al. |
| 2004/0020286 A1 | 2/2004 | Blakely |
| 2004/0022691 A1 | 2/2004 | Allen et al. |
| 2004/0035452 A1 | 2/2004 | Ma |
| 2004/0035462 A1 | 2/2004 | McCarty et al. |
| 2004/0072278 A1 | 4/2004 | Chou et al. |
| 2004/0084370 A1 | 5/2004 | Singh et al. |
| 2004/0084371 A1 | 5/2004 | Kellam et al. |
| 2004/0086427 A1 | 5/2004 | Childers et al. |
| 2004/0125689 A1 | 7/2004 | Ehrfeld et al. |
| 2004/0157096 A1 | 8/2004 | Peterson |
| 2004/0158189 A1 | 8/2004 | Tonelli et al. |
| 2004/0208751 A1 | 10/2004 | Lazar et al. |
| 2004/0215129 A1 | 10/2004 | Edgson et al. |
| 2004/0256230 A1 | 12/2004 | Yager et al. |
| 2005/0006296 A1 | 1/2005 | Sullivan et al. |
| 2005/0007748 A1 | 1/2005 | Callahan et al. |
| 2005/0040110 A1 | 2/2005 | Felding |
| 2005/0070837 A1 | 3/2005 | Ferrarini et al. |
| 2005/0074834 A1 | 4/2005 | Chaplen et al. |
| 2005/0082225 A1 | 4/2005 | Kreymann |
| 2005/0126211 A1 | 6/2005 | Drost et al. |
| 2005/0129580 A1 | 6/2005 | Swinehart et al. |
| 2005/0131332 A1 | 6/2005 | Kelly et al. |
| 2005/0145497 A1 | 7/2005 | Gilbert et al. |
| 2005/0179748 A1 | 8/2005 | Malik et al. |
| 2005/0202557 A1 | 9/2005 | Borenstein et al. |
| 2005/0220681 A1 | 10/2005 | Chang et al. |
| 2006/0046113 A1 | 3/2006 | Wang et al. |
| 2006/0079698 A1 | 4/2006 | Joshi et al. |
| 2006/0157413 A1 | 7/2006 | Bene et al. |
| 2006/0174715 A1 | 8/2006 | Wehrs et al. |
| 2006/0200064 A1 | 9/2006 | Gross et al. |
| 2006/0266692 A1 | 11/2006 | Foster et al. |
| 2007/0020400 A1 | 1/2007 | Chang |
| 2007/0029365 A1 | 2/2007 | Paul et al. |
| 2007/0119771 A1 | 5/2007 | Schukar et al. |
| 2007/0125489 A1 | 6/2007 | Paul et al. |
| 2007/0128707 A1 | 6/2007 | Rorrer et al. |
| 2007/0131403 A1 | 6/2007 | Vetrovec et al. |
| 2007/0149914 A1 | 6/2007 | Axelsson et al. |
| 2007/0158268 A1 | 7/2007 | Decomo |
| 2007/0184576 A1 | 8/2007 | Chang et al. |
| 2007/0215644 A1 | 9/2007 | Otis et al. |
| 2007/0243990 A1 | 10/2007 | Kolenbrander et al. |
| 2007/0278155 A1 | 12/2007 | Lo et al. |
| 2007/0295651 A1 | 12/2007 | Martinez et al. |
| 2008/0006040 A1 | 1/2008 | Peterson et al. |
| 2008/0009780 A1 | 1/2008 | Leonard et al. |
| 2008/0053842 A1 | 3/2008 | Williams et al. |
| 2008/0093298 A1 | 4/2008 | Browning et al. |
| 2008/0097274 A1 | 4/2008 | Neri et al. |
| 2008/0108122 A1 | 5/2008 | Paul et al. |
| 2008/0108930 A1 | 5/2008 | Weitzel et al. |
| 2008/0149563 A1 | 6/2008 | Ash |
| 2008/0196725 A1 | 8/2008 | Mele |
| 2008/0200858 A1 | 8/2008 | Ichiishi et al. |
| 2008/0296226 A1 | 12/2008 | Gotch |
| 2009/0008331 A1 | 1/2009 | Wilt et al. |
| 2009/0012452 A1 | 1/2009 | Slepicka et al. |
| 2009/0038393 A1 | 2/2009 | Chaung et al. |
| 2009/0076433 A1 | 3/2009 | Folden et al. |
| 2009/0087326 A1 | 4/2009 | Voltenburg et al. |
| 2009/0092526 A1 | 4/2009 | Miller |
| 2009/0095679 A1 | 4/2009 | Demers et al. |
| 2009/0101549 A1 | 4/2009 | Kamen et al. |
| 2009/0101576 A1 | 4/2009 | Rohde et al. |
| 2009/0114595 A1 | 5/2009 | Wallenas et al. |
| 2009/0124963 A1 | 5/2009 | Hogard et al. |
| 2009/0165366 A1 | 7/2009 | Jovanovic et al. |
| 2009/0211977 A1 | 8/2009 | Miller |
| 2009/0230036 A1 | 9/2009 | Age et al. |
| 2009/0306573 A1 | 12/2009 | Gagner et al. |
| 2009/0309835 A1 | 12/2009 | Levin et al. |
| 2009/0312686 A1 | 12/2009 | Sakamoto et al. |
| 2009/0320684 A1 | 12/2009 | Weaver et al. |
| 2010/0018923 A1 | 1/2010 | Rohde et al. |
| 2010/0022934 A1 | 1/2010 | Hogard |
| 2010/0051552 A1 | 3/2010 | Rohde et al. |
| 2010/0078385 A1 | 4/2010 | Kawarabata et al. |
| 2010/0089807 A1 | 4/2010 | Heyes et al. |
| 2010/0192686 A1 | 8/2010 | Kamen et al. |
| 2010/0271296 A1 | 10/2010 | Kopychev et al. |
| 2010/0292627 A1 | 11/2010 | Caleffi et al. |
| 2010/0292657 A1 | 11/2010 | Fontanazzi et al. |
| 2010/0292944 A1 | 11/2010 | Howell et al. |
| 2010/0321046 A1 | 12/2010 | Randall et al. |
| 2010/0326914 A1 | 12/2010 | Drost et al. |
| 2010/0326916 A1 | 12/2010 | Wrazel et al. |
| 2011/0005986 A1 | 1/2011 | Kelly et al. |
| 2011/0105979 A1 | 5/2011 | Schlaeper et al. |
| 2011/0106466 A1 | 5/2011 | Furmanski et al. |
| 2011/0132841 A1 | 6/2011 | Rohde et al. |
| 2011/0186517 A1 | 8/2011 | Hedmann et al. |
| 2011/0189048 A1 | 8/2011 | Curtis et al. |
| 2011/0192796 A1 | 8/2011 | Smejtek et al. |
| 2011/0257579 A1 | 10/2011 | Rossi et al. |
| 2011/0295175 A1 | 12/2011 | Felder et al. |
| 2012/0029937 A1 | 2/2012 | Neftel et al. |
| 2012/0065581 A1 | 3/2012 | Childers et al. |
| 2012/0103902 A1 | 5/2012 | Childers et al. |
| 2012/0116316 A1 | 5/2012 | Schutz et al. |
| 2012/0138533 A1 | 6/2012 | Curtis et al. |
| 2012/0204968 A1 | 8/2012 | Fulkerson et al. |
| 2012/0267291 A1 | 10/2012 | Coates |
| 2012/0292246 A1 | 11/2012 | Jovanovic et al. |
| 2012/0318740 A1 | 12/2012 | Ekdahl et al. |
| 2013/0018301 A1 | 1/2013 | Weaver et al. |
| 2013/0020237 A1 | 1/2013 | Wilt et al. |
| 2013/0056419 A1 | 3/2013 | Curtis |
| 2013/0186829 A1 | 7/2013 | Callan et al. |
| 2014/0021111 A1 | 1/2014 | Roger et al. |
| 2014/0069861 A1 | 3/2014 | Browning et al. |
| 2014/0209540 A1 | 7/2014 | Smejtek et al. |
| 2014/0291243 A1 | 10/2014 | Curtis et al. |
| 2015/0314055 A1 | 11/2015 | Hogard et al. |
| 2015/0343128 A1 | 12/2015 | Hogard et al. |
| 2015/0343133 A1 | 12/2015 | Hogard et al. |
| 2015/0354906 A1 | 12/2015 | Miller |
| 2016/0082172 A1 | 3/2016 | Miller et al. |
| 2017/0326285 A1 | 11/2017 | Hogard et al. |
| 2018/0071447 A1 | 3/2018 | Gronau et al. |
| 2019/0022293 A1 | 1/2019 | Peterson et al. |
| 2019/0192758 A1 | 6/2019 | Ritson et al. |
| 2019/0201604 A1 | 7/2019 | Hogard et al. |
| 2020/0061273 A1 | 2/2020 | Hogard et al. |
| 2021/0244869 A1 | 8/2021 | Hogard et al. |
| 2021/0252204 A1 | 8/2021 | Hogard et al. |

FOREIGN PATENT DOCUMENTS

| | | |
|---|---|---|
| DE | 69217519 T2 | 6/1997 |
| EP | 0165751 A2 | 12/1985 |
| EP | 0278100 A2 | 8/1988 |
| EP | 0 324 922 | 7/1989 |
| EP | 0679100 A1 | 11/1995 |
| EP | 0796997 A1 | 9/1997 |
| EP | 0547025 B2 | 6/2002 |
| EP | 1892000 A1 | 2/2008 |
| EP | 1898000 A2 | 3/2008 |

(56) References Cited

FOREIGN PATENT DOCUMENTS

| | | |
|---|---|---|
| EP | 2319551 A2 | 5/2011 |
| EP | 2535067 A1 | 12/2012 |
| GB | 1 289 738 | 9/1972 |
| JP | 59-58002 A | 4/1984 |
| JP | 60-143803 A | 7/1985 |
| JP | H4-35669 A | 2/1992 |
| JP | H11-33111 A | 2/1999 |
| JP | 2001510266 A | 7/2001 |
| JP | 2002143298 A | 5/2002 |
| JP | 2002527212 A | 8/2002 |
| JP | 2003508179 A | 3/2003 |
| JP | 2007167108 A | 7/2007 |
| JP | 2007268490 A | 10/2007 |
| JP | 2007529707 A | 10/2007 |
| JP | 2007327950 A | 12/2007 |
| WO | WO 2005/045894 | 5/1995 |
| WO | WO00/16916 A1 | 3/2000 |
| WO | WO00/25843 A1 | 5/2000 |
| WO | WO00/57935 A1 | 10/2000 |
| WO | WO 2002/040874 | 5/2002 |
| WO | WO 2002/076529 | 10/2002 |
| WO | WO03/076661 A1 | 9/2003 |
| WO | WO2006/011009 A2 | 2/2006 |
| WO | WO2006/039293 A2 | 4/2006 |
| WO | WO 2006/042079 | 4/2006 |
| WO | WO2007/073739 A1 | 7/2007 |
| WO | WO2007/089855 A2 | 8/2007 |
| WO | WO2008/027967 A1 | 3/2008 |
| WO | WO2008/106191 A2 | 9/2008 |
| WO | WO2010/027435 A1 | 3/2010 |
| WO | WO2010/062698 A2 | 6/2010 |
| WO | WO2010/085764 A2 | 7/2010 |
| WO | WO2010/146343 A2 | 12/2010 |

OTHER PUBLICATIONS

Allis and Spencer, "16: Nanostructural Architectures from Molecular Building Blocks," *Handbook of Nanoscience, Engineering, and Technology*, pp. 16-1-16-32, 2003.
Alm, "Diffusion Bonding—Methods and Applications: Part I—Terminology," Systems Group of TRW Inc., *Adhesives Age*, pp. 28-32, Jul. 1970.
Alman et al., "Processing, Structure and Properties of Aluminum-Aluminide Layered Sheet Composites," *Light Weight Alloys for Aerospace Applications III*, The Minerals, Metals & Materials Society, pp. 531-544, 1995.
Alman et al., "Intermetallic Sheets Synthesized from Elemental Ti, Al and Nb Foils," *Metallurgical and Materials Transactions*, 26A:2759-2762, Oct. 1995.
Alman et al., "Fabrication, Structure and Properties of Aluminum-Aluminide Layered Composites," *Materials Research Society Symp. Proc.*, 434:255-260, 1996.
Alman et al., Fabrication of NiAl Intermetallic Reactors for Microtechnology-Based Energy Chemical Systems (MECS), *Transactions of NAMRI/SME*, XXIX:453-459, 2001.
Anglès et al., "Plasticized starch/Tunicin Whiskers Nanocomposite Materials. 2. Mechanical behavior," *Macromolecules*, 34, pp. 2921-2931, 2001.
Battezzati et al., "Solid State Reaction in Al/Ni Alternate Foils Induced by Cold Rolling and Annealing," *Acta Mater.*, 47:1901-1914, 1999.
Battista, "Chapter Two: Microcrystalline Celluloses," *Microcrystal Polymer Science*, McGraw-Hill, New York, NY, pp. 17-57, 1975.
Benson et al., "Process Miniaturization—a Route to Total Environmental Acceptability?" *Trans. IchemE*, 71(Part A):160-168, 1993.
Bower et al., "Aligned Wafer Bonding: a Key to Three Dimensional Microstructures," *Journal of Electronic Materials*, 20:383-387, 1991.
Chazeau et al., "Mechanical behaviour above $T_g$ of a plasticised PVC reinforced with cellulose whiskers; a SANS structural study," *Polymer*, vol. 40, pp. 5333-5344, 1999.

Colgan, "A Review of Thin-Film Aluminide Formation," *Material Science Reports* 5:1-44, North-Holland, Jan. 1990.
Cuta et al., "Fabrication and testing of microchannel heat exchangers," *SPIE Conf.*, 2640:152-160, 1995.
D'Heurle, "Reactive Diffusion in a Prototype System: Nickel-Aluminum I: Non-Constant Diffusion Coefficient," *Thin Solid Films*, 215:19-25, 1992.
De Souza Lima et al., "Rodlike Cellulose Microcrystals: Structure, Properties, and Applications," *Macromolecular Rapid Communications*, vol. 25, pp. 771-787, 2004.
Deevi et al., "Processing, Properties and Applications of Nickel and Iron Aluminides," *Progress in Materials Science*, 42:177-192, 1997.
Demura et al., "Ductile Thin Foil of $Ni_3Al$," *Mechanical Properties of Structural Films*, 11-12:248-261, 2000.
Demura et al., "Fabrication of $Ni_3Al$ Thin Foil by Cold-Rolling," *Intermetallics*, 9:157-167, 2001.
Derby et al., "Theoretical Model for Diffusion Bonding," *Metal Science*, 16:49-56, Jan. 1982.
Dunford et al., "Diffusion Bonding of Al—Li Alloys," *Materials Science and Technology*, 8:385-398, May 1992.
Duszczyk et al., "The Characteristics of the Diffusion Between the As-Reaction-Formed $Ni_3Al$ Intermetallic Compound and Pure Nickel for Interfacial Bonding," *Journal of Materials Science Letters*, 18:111-113, 1999.
Ehrfeld et al., "Characterization of mixing in micromixers by a test reaction: Single mixing units and mixer arrays," *Ind. Eng. Chem. Res.* 38(3):1075, 1999.
Esposito, *Fluid Power with Applications*, Prentice Hall, pp. 380-381, 1988.
Favier et al., "Nanocomposite Materials from Latex and Cellulose Whiskers," *Polymers for Advanced Technologies* 6:351-355, 1995.
Favier et al., "Mechanical Percolation in Cellulose Whisker Nanocomposites," *Polymer Engineering and Science*, vol. 37, pp. 1732-1739, 1997.
Fischer et al., "Manufacturing of Aluminum Nitride Heat Exchangers by Ceramic Injection Molding," *Ceramic Engineering and Science Proceedings*, 20(4):595-602, 1999.
Garmong et al., "Attainment of Full Interfacial Contact During Diffusion Bonding," *Metallurgical Transactions*, 6A:1269-1279, Jun. 1975.
George et al., "Ordered Intermetallics," *Annu. Rev. Mater. Sci.*, 24:409-451, 1994.
Glatz et al., "Diffusion Bonding of Intermetallic Ti—47Al—2Cr—0—2Si Sheet Material and Mechanical Properties of Joints at Room Temperature and Elevated Temperatures," *Intermetallics*, 5:415-423, Sep. 1997.
Goldberg, "Narrow Channel Forced Air Heat Sink," *IEEE Transactions on Components, Hybrids, and Manufacturing Technology*, CHMT-7(1):154-159, Mar. 1984.
Grunert et al., "Progress in the Development of Cellulose Reinforced Nanocomposites," *Polymeric Materials: Science and Engineering*, Abstracts of papers, Abstract No. 126, 2000.
Grunert et al., "Cellulose Nanocrystal Reinforced Cellulose Acetate Butyrate Nanocomposites," *Polymeric Materials: Science and Engineering*, vol. 86, pp. 367-368, 2002.
Haas et al., "Fabrication and Performance of MMW and SMMW Platelet Horn Arrays," *Intl. J. Infrared and Millimeter Waves*, 14(11):2289-2293, 1993.
Haas, "Further development of MMW and SMMW platelet feed horn arrays," *Astron. Soc. Pac. Conf. Ser.*, 75:99-105, 1995.
Herschberg, "Manufacturing Technology of the Tektronix Digital Ink Jet Head," *SPSE 3rd International Congress on Advances in Non-Impact Printing Technologies, Journal of Imaging Technology*, 14:124-128, 1998.
Hessel et al., "High Temperature HCN Generation in an Integrated Microreaction System," *Proc. IMRET3*, Frankfurt, Germany, pp. 151-164, Apr. 1999.
Hill et al., "Modelling Solid-State Diffusion Bonding," *Acta Metal. Mater.*, 37(9):2425-2537, 1989.
Humpston et al., "Principles in Soldering and Brazing, 4.4.2. Diffusion Soldering and Brazing," *ASM International*, pp. 128-143, 1993.

(56) References Cited

OTHER PUBLICATIONS

Islam et al., "Effect of Surface Finish and Sheet Thickness on Isostatic Diffusion Bonding of Superplastic Ti—6Al—4V," *Materials Science and Technology*, 13:1045-1050, Dec. 1997.

Islam et al., "Isostatic Diffusion Bonding of a Microduplex Stainless Steel," *Scripta Materialia*, 38(8):1187-1193, 1998.

Jacobson et al., "Diffusion Soldering," *Soldering and Surface Mount Technology*, Chap. 10, pp. 27-32, Feb. 1992.

Kao et al., "A Theoretical Analysis for the Formation of Periodic Layered Structure in Ternary Diffusion Couples Involving a Displacement Type of Reaction," *Acta. Metal. Mater.*, 41(12):3463-3472, 1993.

Khan et al., "Transient liquid phase diffusion bonding and associated recrystalization phenomenon when joining ODS ferritic superalloys,"*J Mat. Sci.*, 31:2937-2943, Jun. 1996.

Kleiner, "High Performance Forced Air Cooling Scheme Employing Microchannel Heat Exchangers," *IEEE Transactions on Components, Packaging, and Manufacturing Technology*, 18(4):795-804, Dec. 1995.

Knight, "Optimal Thermal Design of Air Cooled Forced Convection Finned Heat Sinks-Environmental Verification," *IEEE Transactions on Components, Hybrids, and Manufacturing Technology*, 15:754-760, 1992.

Koeneman et al., "Feasibility of Micro Power Supplies for MEMS," *J. MicroElectoMechanical Sys*, 6(4):355-362, 1997.

Krause et al., "Microchannel coolers for high power laser diodes in copper technology," *Proc. SPIE*, 2148:351-385, 1994.

Ling et al., "Passive Alignment and its Application in Multi-level X-ray Lithography," *Materials and Device Characterization in Micromachining III, Proceedings of SPIE*, 4175:43-49, 2000.

Little, "Microminiature Refrigerators for Joule-Thomson Cooling of Electronic Chips and Devices," *Advances in Cryogenic Engineering*, 35:1325-1333, 1990.

Liu et al., "Ordered Intermetallic Alloys, Part I: Nickel and Iron Aluminites," *Journal of Minerals, Metals, and Materials Society*, 45(5):38-44, May 1993.

Lopez et al., "Microstructural analysis of steel-nickel alloy clad interfaces," *Mat. Sci. and Tech.*, pp. 45-55, Jan. 1996.

Martin et al., "Microchannel heat exchangers for advanced climate control," *Proc. SPIE*, 2639:82-88, 1995.

Paul et al., "Limits on Aspect Ratio in Two-fluid Micro-scale Heat Exchangers," *Transactions of NAMRI XXIX*, Gainesville, Florida, 2001.

Paul et al., "An Evaluation of Two Methods for Producing Intermetallic Microchannels," *Proceedings of IMEC*, pp. 261-266, ASME International Mechanical Engineering Congress of Exposition, New Orleans, Louisiana, Nov. 17-22, 2002.

Raviprasad et al.., "Layered Structures Produced by Rolling Dissimilar Metals," *Journal of Materials Science Letters*, 15:511-514, 1996.

Martin et al., "Microfabrication methods for microchannel reactors and separations systems," *Pacific Northwest National Laboratory*, 8 pages, 1997.

Martin et al., "Microfabrication Methods for Microchannel Reactors and Separations Systems," *Chem. Eng. Comm.*, 173:245-254, 1999.

Matson, "Laser micromachined microchannel solvent separator," *SPIE*, 3223:253-259, 1997.

Matson et al., "Fabrication of Microchannel Chemical Reactors Using a Metal Lamination Process," *Proc. IMRET3*, 10 pages, Frankfurt, Germany, Apr. 1999.

Michaelson et al., "The Early Stages of Solid-State Reactions in Ni/Al Multilayer Films," *J. Appl. Phys.*, 80(12):6689-6698, Dec. 1996.

Moore et al., "Diffusion Brazing NiAl with Self-Generated Filler Metal," *Materials Research Society, Mat. Res. Soc. Symp. Proc.*, 288:1173-1178, 1993.

Morin et al., "Nanocomposites of Chitin Whiskers from *Riftia* Tubes and Poly(caprolactone)," *Macromolecules*, vol. 35, pp. 2190-2199, 2002.

Nakamura et al., "Research on Pressure Welding Conditions of Various Work Metals (Effects of Contact Pressure, Surface Expansion Ratio and Temperature)," *JSME International Journal*, Series III 31(3):612-617, 1988.

Nakao et al., "Diffusion Bonding of Intermetallic Compound TiAl," *ISIJ International*, 31(10):1260-1266, 1991.

Nasa, "National Space Transportation System Shuttle Reference Manual," p. 8, located at www.ksc.nasa.gov/shuttle/technology/sts-newsref/sts-oms.html, 1988.

Oddy et al., "Electrokinetic Instability Micromixing," *Anal. Chem.*, 73:5822-5832, 2001.

Orhan et al., "A New Model for Diffusion Bonding and its Application to Duplex Alloys," *Materials Science and Engineering*, A271:458-468, 1999.

Orts et al., "Effect of Fiber Source on Cellulose Reinforced Polymer Nanocomposites," Annual Technical Conference—Society of Plastics Engineers, $62^{nd}$, pp. 2427-2431, (2 pages) 2004.

Paillet et al., "Chitin Whisker Reinforced Thermoplastic Nanocomposites," *Macromolecules*, vol. 34, No. 19, pp. 6527-6530, 2001.

Paransky et al., "Kinetics of Two-Phase Layer Growth During Reactive Diffusion," *Materials Science and Engineering*, A270: 231-236, 1999.

Paul et al., "Microlamination for Microtechnology-based Energy, Chemical, and Biological Systems," *ASME IMECE* 39:45-52, Nashville, Tennessee, Nov. 15-20, 1999.

Paul et al., "Intermetallic Microlamination for High-Temperature Microreactors," 4th Int. Conf. Microreaction Tech., Atlanta, Georgia, pp. 236-243, American Institute of Chemical Engineers [AIChE], Mar. 5-9, 2000.

Paul et al., "Understanding Limits on Fin Aspect Ratios in Counterflow Microchannel Arrays Produced by Diffusion Bonding," *J. Manuf. Sci. Eng.*, 128(4):977, Nov. 2006.

Peterson, "Size Limits for Regenerative Heat Engines," *Microscale Thermophysical Engineering*, 2:121-131, 1998.

Peterson et al.., "Numerical Modeling of Conduction Effects in Microscale Counterflow Heat Exchangers," *Microscale Thermophysical Engineering*, 3:17-30, 1999.

Philibert, "Reactive Diffusion in Thin Films," *Applied Surface Sciences*, 53:74-81, North-Holland, 1991.

Pilling, "The Kinetics of Isostatic Diffusion Bonding in Superplastic Materials," *Materials Science and Engineering*, 100:137-144, 1988.

Pilling, "On the Modeling of Diffusion Bonding in Materials: Superplastic Super Alpha-2," *Materials Science and Engineering* A205:72-78, 1996.

Pluess, "Application of Controlled Thermal Expansion in Diffusion Bonding for the High-Volume Microlamination of MECS Devices," Thesis (MS)—Oregon State University, 2004.

Pluess et al., "Application of Controlled Thermal Expansion in Microlamination for the Economical Production of Bulk Microchannel Systems," *Chem. Engr. Comm.*, 194:1259-1270, 2007.

Porter et al., "Cost Drivers in Microlamination Based on a High-Volume Production System Design," *Proceedings of IMECE 2002, ASME International Mechanical Engineering Congress & Exposition*, Nov. 17-22, 2002, New Orleans, Louisiana.

PowerPoint slides presented at $4^{th}$ International Conference of Microreaction Technology, Atlanta, Georgia, Mar. 5-9, 2000.

Revol et al., "Cellulose-based Chiral Nematic Structures," in *Cellulosics: Chemical, Biochemical and Material Aspects*, Eds J.F. Kennedy, G.O. Phillips and P.A. Williams, Ellis Horwood, New York, pp. 115-122, 1993.

Ridley et al., "Isostatic diffusion bonding of microduplex stainless steel," *Mat. Sci. and Tech.*, 8: 791-795, Sep. 1992.

Robertson et al., "In Situ Interferometric Alignment Systems for the Assembly of Microchannel Relay Systems," *Applied Optics*, 36:9253-9260, 1997.

Rode et al., "Self-Aligned Positioning of Microoptical Components by Precision Prismatic Grooves Impressed in Metal," *IEEE Journal of Microelectromechanical Systems*, 8:58-64, Mar. 1999.

Ruiz et al., "Processing and characterization of new thermoset nanocomposites based on cellulose whiskers," *Composite Interfaces*, vol. 7, No. 2, pp. 117-131, 2000.

(56) References Cited

OTHER PUBLICATIONS

Schwab et al., "Molecular Rods. 1. Simple Axial Rods," *Chemical Reviews*, 99(7):1863-1933, 1999.
Sharma et al., "The Application of Surface Mount Technology to Multi-Scale Process Intensification," *ASPE*, pp. 1-4, Oct. 2003.
Spadaccini et al.., "Development of a Catalytic Silicon Micro-Combustor for Hydrocarbon-Fueled Power Mems," *The Fifteenth IEEE International Conference on Micro Electro Mechanical Systems*, pp. 228-231, Las Vegas, Nevada, Jan. 20-24, 2002.
Stroock et al., "Chaotic Mixer for Microchannels," *Science*, 295:647-651, 2002.
Strum et al.., "Liquid-Assisted Diffusion Bonding of NiAl," *Advanced Joining Technologies for New Materials II*, Conference Proceedings, pp. 76-88, Mar. 1994.
"Technology Development Through Industrial Partnerships," *Federal Energy Technology Center*, Oct. 1997.
Tour, "Chapter 3: Chemical Synthesis," *Molecular Electronics, Commercial Insights, Chemistry, Devices, Architecture and Programming*, World Scientific, pp. 33-41, Mar. 2003.
Uenishi et al.., "Joining of Intermetallic Compound TiAl by Using Al Filler Metal," *Zeitschrift fur Metallkunde*, 86(4):270-274, 1995.
Van Loo et al., "Solid State Diffusion and Reactive Phase Formation," *Solid State Ionics*, 95:95-106, 1997.
Wang et al., "Ni—$Al_2O_3$ and Ni—Al Composite High-Aspect-Ratio Microstructures," *Materials and Device Characterization in Micromachining*, 3512:344-352, 1998.
Wattanutchariaya et al., "Bonding Fixture Tolerances for High-Volume Metal Microlamination Based on Fin Buckling and Lamina Misalignment Behavior," *J. Intl Soc of Precision Engr and Nanotechnology*, 2002.
Wegeng et al., "Energy systems miniaturization technologies, devices, and systems," *Proceedings of the International Symposium on Advanced Energy Conversion Systems and Related Technologies* (RAN95), 8 pages, Dec. 1995.
Wegeng et al., "Chemical system miniaturization," *Proceedings of the AIChE Spring National Meeting*, pp. 1-13, Feb. 1996.
Welding Institute, http://www.twi.co.uk/j32k/protected/band_3/ksab001.html, accessed on Feb. 22, 2008.
Wu et al., "Superplastic Forming/Diffusion Bonding of Laser Surface Melted TiAl Intermetallic Alloy," *Scripta Materialia*, 45:895-899, 2001.
Yussuf et al., "Microwave Welding of Polymeric-Microfluidic Devices," *Micromec. Microeng.*, 15:1692-1699, 2005.
International Search Report dated Sep. 16, 2010, from International Patent Application No. PCT/US2010/037621.
Chinese State Intellectual Property Office Action dated Feb. 20, 2009, in Chinese Patent Application No. CN 200580041446.8.
U.S. Appl. No. 09/369,679—Office Action dated Jun. 22, 2001.
U.S. Appl. No. 09/369,679—Office Action dated Apr. 11, 2002.
U.S. Appl. No. 09/369,679—Office Action dated Dec. 6, 2002.
U.S. Appl. No. 09/996,621—Office Action dated May 16, 2003.
U.S. Appl. No. 10/576,963—Office Action dated Jan. 29, 2009.
U.S. Appl. No. 10/576,963—Office Action dated Jul. 28, 2009.
U.S. Appl. No. 10/576,963—Office Action dated Jan. 25, 2010.
U.S. Appl. No. 10/803,502—Office Action dated Jun. 6, 2008.
U.S. Appl. No. 10/803,502—Office Action dated Mar. 30, 2009.
U.S. Appl. No. 10/803,502—Office Action dated Oct. 21, 2009.
U.S. Appl. No. 11/086,074—Office Action dated Apr. 1, 2008.
U.S. Appl. No. 11/243,937—Office Action dated Apr. 15, 2009.
U.S. Appl. No. 11/243,937—Office Action dated Sep. 20, 2010.
U.S. Appl. No. 11/490,966—Office Action dated Jul. 21, 2008.
U.S. Appl. No. 11/490,966—Office Action dated Oct. 21, 2008.
U.S. Appl. No. 11/517,731—Office Action dated Jun. 6, 2008.
U.S. Appl. No. 11/517,731—Office Action dated Aug. 29, 2008.
U.S. Appl. No. 11/576,804—Office Action dated Jun. 10, 2010.
U.S. Appl. No. 11/576,804—Notice of Allowance dated Nov. 29, 2010.
U.S. Appl. No. 14/808,827—Office Action dated Sep. 12, 2017.
U.S. Appl. No. 14/808,827—Office Action dated Jan. 17, 2018.
U.S. Appl. No. 14/808,827—Notice of Allowance dated Jun. 22, 2018.
U.S. Appl. No. 16/13 8,441—Office Action dated Apr. 29, 2020.
California Energy Commission; Development of Supported Polymeric Liquid Membrane Technology for Aqueous MTBF Mitigation, EPRI, Palo Alto, CA, California Energy Commission, Sacramento. CA: Doc. No. 1006577; 70 pgs.; Jul. 2002.
Introtek International; Drip chamber liquid level sensor (sales literature); 2 pages; retrieved from the internet (http://www.introtek.com/PDFs/1/DDS-14.0_DripDetectSensor.pdf); © Jan. 1, 2009.
Omega Engineering Inc.; Load Cell (definition, information); 3 pgs; retrieved from the internet on Jun. 17, 2015 (http://www.omega.com/prodinfo/LoadCells.html).
Thorsen et al.; Microfluidic Large-Scale Integration; Science; 298; pp. 580-584; Oct. 18, 2002.
Hogard et al.; U.S. Appl. No. 17/395,281 entitled "Dialysis system and methods," filed Aug. 5, 2021.
Hu et al.; U.S. Appl. No. 17/522,778 entitled "Dialysis system and methods," filed Nov. 9, 2021.
Ritson et al.; U.S. Appl. No. 18/059,181 entitled "Peritoneal Dialysis System and Methods," filed Nov. 28, 2022.

* cited by examiner

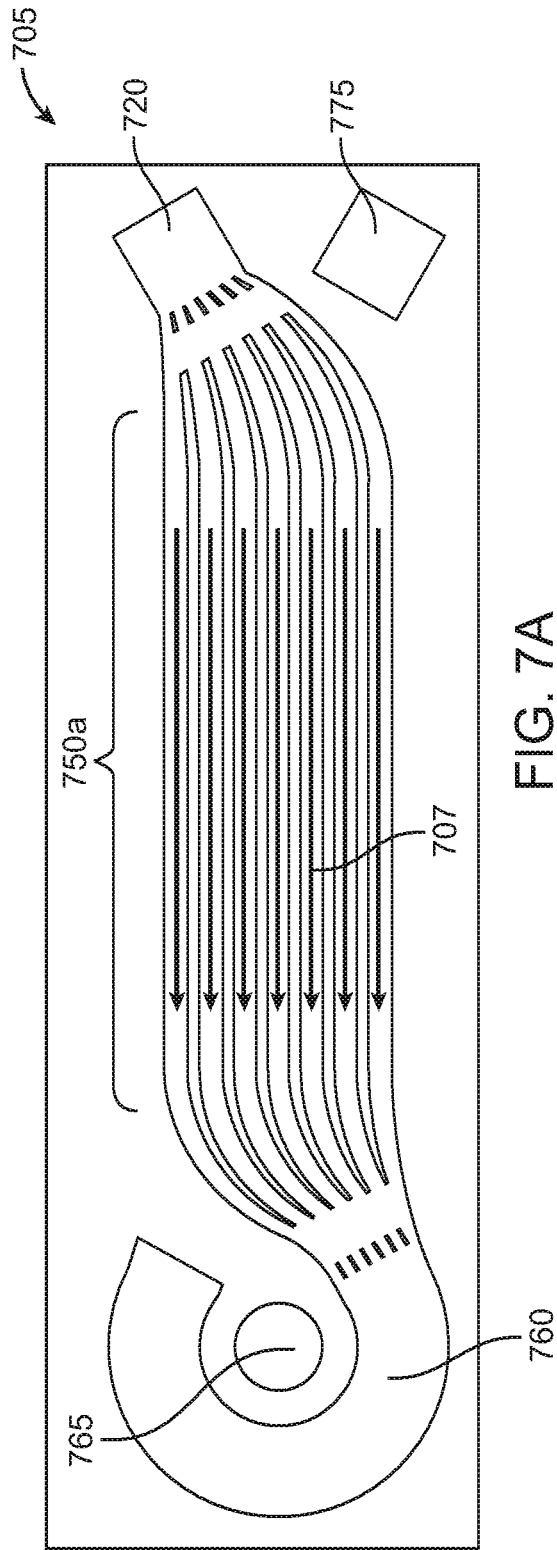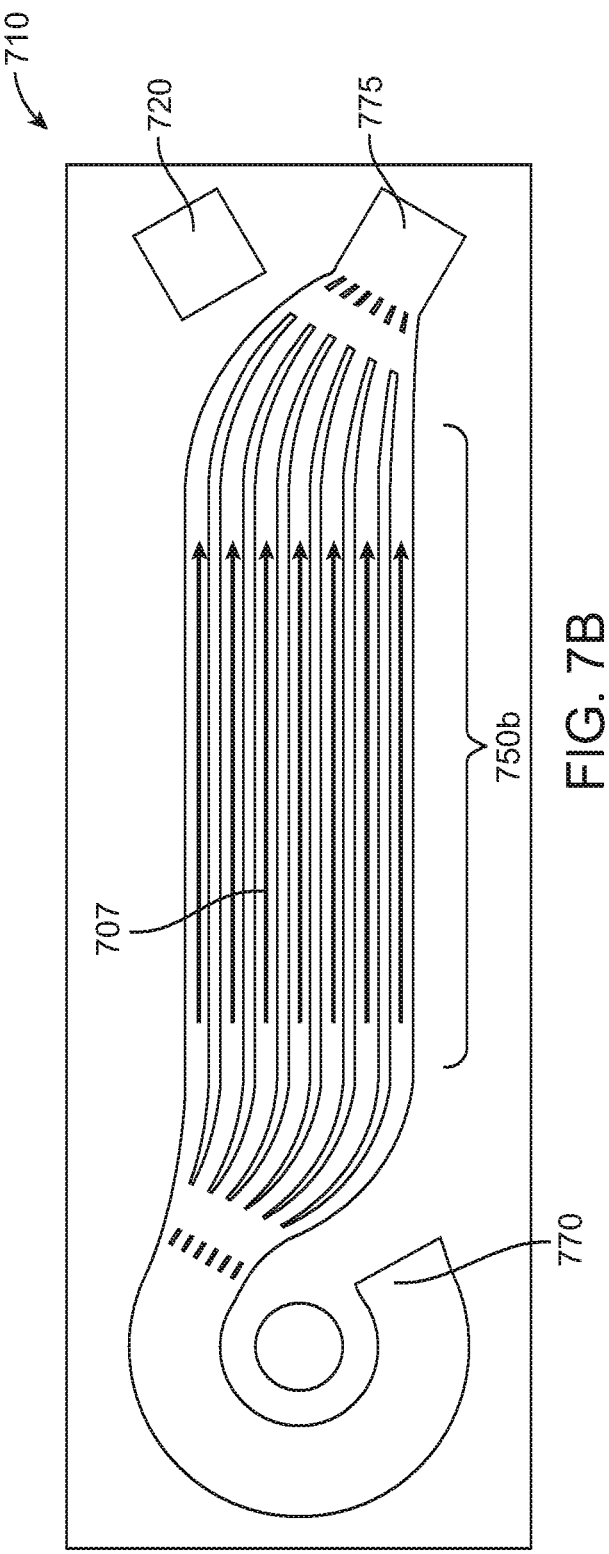
FIG. 7A
FIG. 7B

| Temperature | Time | Pasteurization Type |
|---|---|---|
| 63°C (145°F) | 30 minutes | Vat Pasteurization |
| 72°C (161°F) | 15 seconds | High Temperature Short Time Pasteurization (HTST) |
| 89°C (191°F) | 1.0 second | Higher-Heat Shorter Time Pasteurization (HHST) |
| 90°C (194°F) | 0.5 second | Higher-Heat Shorter Time Pasteurization (HHST) |
| 94°C (201°F) | 0.1 second | Higher-Heat Shorter Time Pasteurization (HHST) |
| 96°C (204°F) | 0.05 second | Higher-Heat Shorter Time Pasteurization (HHST) |
| 100°C (212°F) | 0.01 second | Higher-Heat Shorter Time Pasteurization (HHST) |
| 138°C (280°F) | 2.0 seconds | Ultra High Temperature Pasteurization (UHT) |

FIG. 14

FLUID PURIFICATION SYSTEM

This is a divisional of U.S. patent application Ser. No. 16/138,441, filed Sep. 21, 2018 (abandoned), which is a divisional of U.S. patent application Ser. No. 14/808,827, filed on Jul. 24, 2015, now issued as U.S. Pat. No. 10,105,476, which is a continuation of U.S. patent application Ser. No. 13/965,720, filed Aug. 13, 2013, now issued as U.S. Pat. No. 9,138,687, which is a continuation of U.S. patent application Ser. No. 13/068,038, filed Apr. 29, 2011, now issued as U.S. Pat. No. 8,524,086, which is a continuation of U.S. patent application Ser. No. 12/795,382, filed Jun. 7, 2010, now issued as U.S. Pat. No. 8,501,009. These prior applications are incorporated herein by reference in their entirety.

FIELD

The present disclosure concerns a fluid purification system, particularly a liquid purification system, and even more particularly a system for preparing fluids for use in dialysis.

BACKGROUND

There are, at present, hundreds of thousands of patients in the United States with end-stage renal disease. Most of those require dialysis to survive. United States Renal Data System projects the number of patients in the U.S. on dialysis will climb past 600,000 by 2012. Many patients receive dialysis treatment at a dialysis center, which can place a demanding, restrictive and tiring schedule on a patient. Patients who receive in-center dialysis typically must travel to the center at least three times a week and sit in a chair for 3 to 4 hours each time while toxins and excess fluids are filtered from their blood. After the treatment, the patient must wait for the needle site to stop bleeding and blood pressure to return to normal, which requires even more time taken away from other, more fulfilling activities in their daily lives. Moreover, in-center patients must follow an uncompromising schedule as a typical center treats three to five shifts of patients in the course of a day. As a result, many people who dialyze three times a week complain of feeling exhausted for at least a few hours after a session.

Given the demanding nature of in-center dialysis, many patients have turned to home dialysis as an option. Home dialysis provides the patient with scheduling flexibility as it permits the patient to choose treatment times to fit other activities, such as going to work or caring for a family member. One requirement of a home dialysis system is a reliable water purification system as dialysis requires purified water for mixing with a dialysate concentrate. Even trace amounts of mineral concentrates and biological contamination in the water can have severe adverse effects on a dialysis patient. In addition, water purification systems in typical dialysis systems must be capable of purifying the very large quantities of water required to run a full dialysis session.

Unfortunately, existing water purifications have drawbacks that limit practical usage of such systems in a home dialysis system. Existing water purification systems are large and bulky, often being as large as a residential washing machine and weighing over three hundred pounds. Such systems also very often consume large amounts of energy in order to purify relatively small amounts of water. In sum, existing water purification systems are bulky and expensive, making them practically unsuitable for use in the average patient's home.

SUMMARY

In view of the foregoing, there is a need for improved water purification systems that may be used in conjunction with home dialysis. Such a system would ideally be small, lightweight, portable, and have the capability of reliably, reproducibly, highly efficiently and relatively inexpensively providing a source of purified water of sufficient volumes to enable home dialysis. In addition, such a water purification system could ideally be incorporated into a dialysis system that requires much less purified water at any one time than the volumes typically needed for dialysis today, thereby further reducing the expense of running the system at home. In addition, the system would be capable of producing real-time, on-demand ultrapure water for dialysis, the gold standard of present-day dialysis. Disclosed herein is an in-line, non-batch water purification system that utilizes a microfluidics heat exchanger for heating, purifying and cooling water. The system is compact and light-weight relative to existing systems and consumes relatively low amounts of energy. The water purification system is suitable for use in a home dialysis system although it can be used in other environments where water purification is desired. The system can also be used to purify fluids other than water. The system can be connected to a residential source of water (such as a running water tap to provide a continuous or semi-continuous household stream of water) and can produce real-time pasteurized water for use in home dialysis, without the need to heat and cool large, batched quantities of water.

In one aspect, disclosed is a method of preparing dialysate for use in a dialysis system. The method includes coupling a water source, such as a household water stream, to a dialysis system; filtering the water stream; heating the water stream to at least about 138 degrees Celsius in a non-batch process to produce a heated water stream; maintaining the heated water stream at or above at least about 138 degrees Celsius for at least about two seconds; cooling the heated water stream to produce a cooled water stream; ultrafiltering the cooled water stream; and mixing dialysate components into the cooled water stream in a non-batch process.

In another aspect, disclosed is a method of preparing dialysate for use in a dialysis system that includes processing a household water stream in a non-batch process to produce an ultra-high-temperature-pasteurized water stream; and mixing dialysate components into said ultra-high-temperature-pasteurized water stream. The mixing of dialysate components is performed in a non-batch process.

In another aspect, disclosed is a method of ultrapasteurizing a fluid including providing a microfluidic heat exchanger having a fluid flowpath for only a single fluid. The flowpath includes multiple fluid pathways for said single fluid to travel. The fluid flowpath includes an inlet portion, a heating portion and an outlet portion that thermally communicates with the inlet portion when the heat exchanger is in operation. The method also includes introducing the fluid into the inlet portion of the heat exchanger at a selected flow rate; transferring heat to the fluid in the inlet portion from the fluid in the outlet portion, thereby heating the fluid in the inlet portion and cooling the fluid in the outlet portion; further heating the fluid in the heating portion to a temperature greater than about 130 degrees Celsius; maintaining the fluid at a temperature greater than about 130 degrees Celsius for a period of at least about two seconds at the selected flow rate; and cooling the fluid in the outlet portion at least in part by the transfer of heat to the fluid in the inlet portion, and permitting the fluid to exit the microfluidic heat exchanger without interaction with a second fluid within the heat exchanger.

In another aspect, disclosed is a fluid purification system including a fluid pathway having an inlet where fluid flows into the system and an outlet where fluid flows out of the system. The fluid pathway further includes a first region where fluid flows in a first direction at a first temperature; a heater region downstream of the first region; and a second region downstream of the heater region where fluid flows in a second direction at a temperature greater than the first temperature. The heater region includes at least one heater that transfers heat into fluid flowing through the heater region to increase the temperature of fluid flowing in the heater region to a second temperature greater than the first temperature. Fluid flowing in the second region thermally communicates with fluid flowing in the first region such that heat transfers from fluid flowing in the second region to fluid flowing in the first region resulting in a temperature reduction in the fluid as it flows through the second region. Fluid flows out of the pathway through the outlet at a temperature less than the second temperature.

Other features and advantages should be apparent from the following description of various embodiments, which illustrate, by way of example, the principles of the disclosed devices and methods.

BRIEF DESCRIPTION OF THE DRAWINGS

FIG. 7A shows a plan view of another embodiment of an inlet lamina.

FIG. 7B shows a plan view another embodiment of an outlet lamina.

FIG. 14 is a table illustrating combinations of temperature and time to achieve various pasteurization levels.

DETAILED DESCRIPTION

In order to promote an understanding of the principals of the disclosure, reference is made to the drawings and the embodiments illustrated therein. Nevertheless, it will be understood that the drawings are illustrative and no limitation of the scope of the disclosure is thereby intended. Any such alterations and further modifications in the illustrated embodiments, and any such further applications of the principles of the disclosure as illustrated herein are contemplated as would normally occur to one of ordinary skill in the art.

Figure 1:
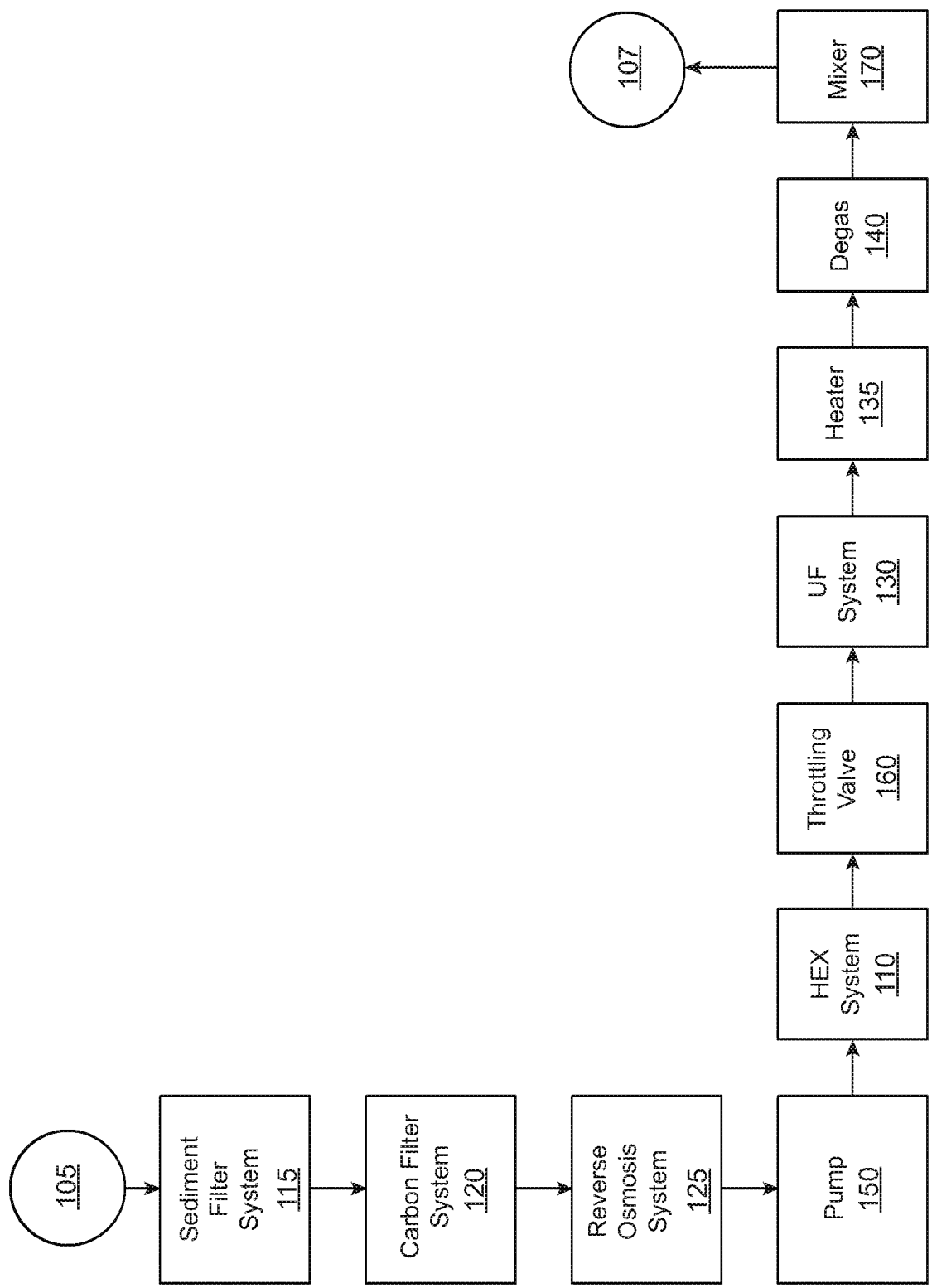
FIG. 1 shows a high level, schematic view of a fluid purification system adapted to purify a fluid such as a liquid.

FIG. 1 shows a high level, schematic view of a fluid purification system adapted to purify a fluid such as a liquid. In an embodiment, the system is adapted to be used for purifying water, such as water obtained from a household tap, in a dialysis system and is sometimes described herein in that context. However, it should be appreciated that the fluid purification system can be used for purifying water in other types of systems and is not limited for use in a dialysis system. Also, the purification system can be used to purify liquids other than water.

With reference to FIG. 1, the fluid purification system includes a plurality of subsystems and/or components each of which is schematically represented in FIG. 1. A fluid such as water enters the fluid purification system at an entry location 105 and communicates with each of the subsystems and components along a flow pathway toward an exit location 107. Upon exiting the fluid purification system, the fluid is in a purified state. This may include the fluid being in a pasteurized state although the fluid system does not necessarily pasteurize the fluid in all circumstances. The embodiment shown in FIG. 1 is exemplary and not all of the components shown in FIG. 1 are necessarily included in the system. The individual components included in the system may vary depending on the type and level of purification or pasteurization required. The quantity and sequential order of the subsystems along the flow pathway shown in FIG. 1 is for purposes of example and it should be appreciated that variations are possible.

The fluid purification system includes at least one microfluidic heat exchange (HEX) system 110 adapted to achieve pasteurization of the liquid passing through the fluid purification system, as described more fully below. The fluid purification system may also include one or more additional purification subsystems, such as a sediment filter system 115, a carbon filter system 120, a reverse osmosis system 125, an ultrafilter system 130, an auxiliary heater system 135, a degassifier system 140, or any combination thereof. The fluid purification system may also include hardware and/or software to achieve and control fluid flow through the fluid purification system. The hardware may include one or more pumps 150 or other devices for driving fluid through the system, as well as sensors for sensing characteristics of the fluid and fluid flow. The operation of the fluid purification system is described in detail below.

Microfluidic Heat Exchange System

Figure 2:
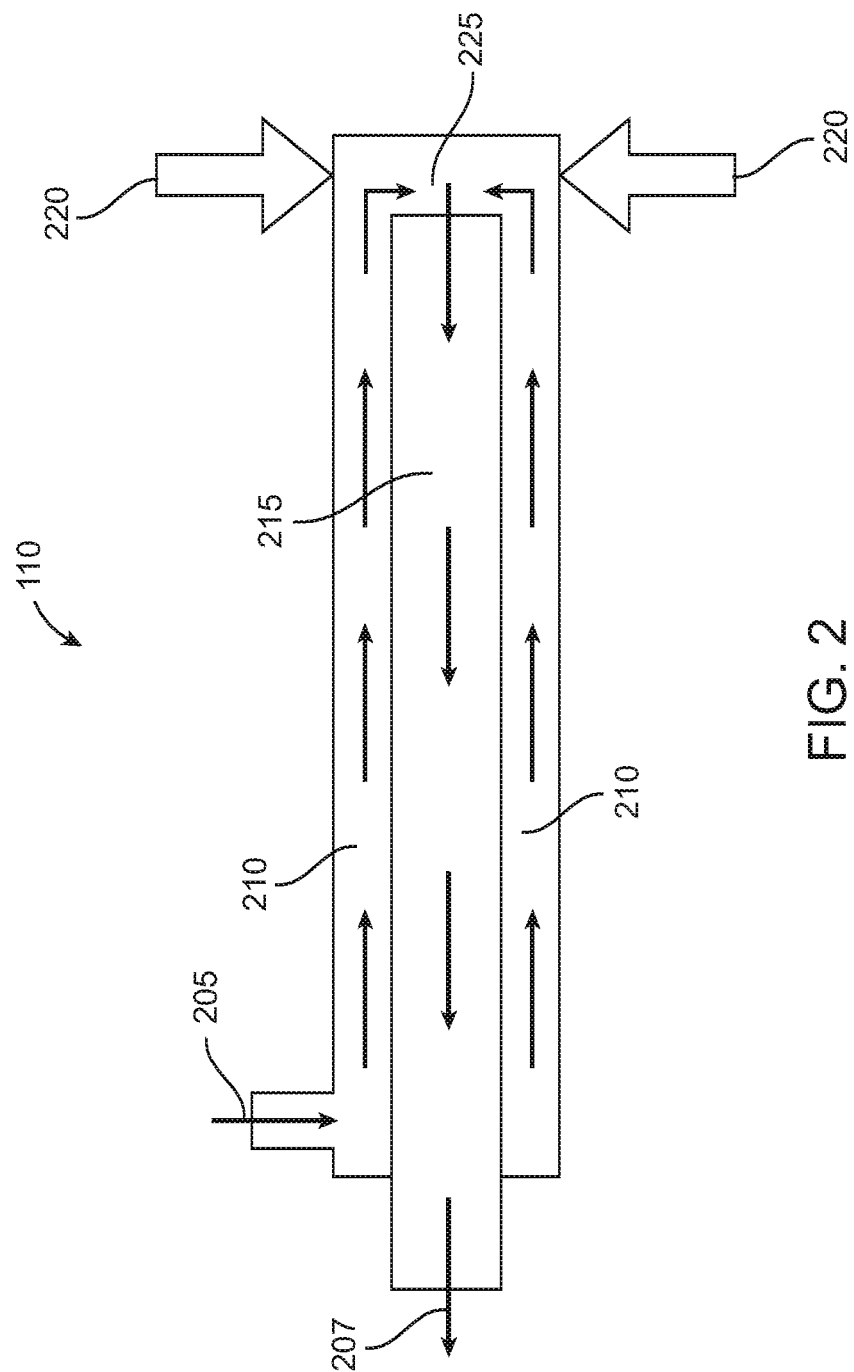
FIG. 2 shows a schematic, plan view of an exemplary embodiment of a microfluidic heat exchange system adapted to heat and cool a single fluid without the use of a second fluid stream to add heat to or remove heat from the fluid.

FIG. 2 shows a schematic, plan view of an exemplary embodiment of the microfluidic heat exchange system 110, which is configured to achieve pasteurization of a liquid (such as water) flowing through the system without the need for a second fluid stream to add heat to or remove heat from the liquid. FIG. 2 is schematic and it should be appreciated that variations in the actual configuration of the flow pathway, such as size and shape of the flow pathway, are possible.

As described more fully below, the microfluidic heat exchange system defines a fluid flow pathway that includes (1) at least one fluid inlet; (2) a heater region where incoming fluid is heated to a pasteurization temperature via at least one heater; (3) a residence chamber where fluid remains at or above the pasteurization temperature for a predetermined time period; (4) a heat exchange section where incoming fluid receives heat from hotter (relative to the incoming fluid) outgoing fluid, and the outgoing fluid cools as it transfers heat to the incoming fluid; and (5) a fluid outlet where outgoing fluid exits in a cooled, pasteurized state. Depending on the desired temperature of the outgoing fluid, one or more additional heat exchanges may be required downstream to adjust the actual temperature of the outgoing fluid to the desired temperature for use, for example, in dialysis. This is especially true in warmer climates, where incoming water may be tens of degrees higher than water supplied in colder climates, which will result in higher outlet temperatures than may be desired unless further cooling is applied. In an embodiment, the flow pathway is at least partially formed of one or more microchannels, although utilizing microfluidic flow fields as disclosed in U.S. Provisional Patent Application No. 61/220,117, filed on Jun. 24, 2009, and its corresponding utility application entitled "Microfluidic Devices," filed Jun. 7, 2010, and naming Richard B. Peterson, James R. Curtis, Hailei Wang, Robbie Ingram-Gobel, Luke W. Fisher and Anna E. Garrison, incorporated herein by reference, for portions of the fluid flow pathway such as the heat exchange section is also within the scope of the invention. The relatively reduced dimensions of a microchannel enhance heat transfer rates of the heat exchange system by providing a reduced diffusional path length and amount of material between counterflow pathways in the system. In an embodiment, a microchannel has at least one dimension less than about 1000 µm. The dimensions of a microchannel can vary and are generally engineered to achieve desired heat transfer characteristics. A microchannel in the range of about 0.1 to about 1 mm in hydraulic diameter generally achieves laminar fluid flow through the microchannel, particularly in a heat exchange region of the microchannel. The small size of a microchannel also permits the heat exchange system 110 to be compact and lightweight. In an embodiment, the microchannels are formed in one or more lamina that are arranged in a stacked configuration, as formed below.

The flow pathway of the microfluidic heat exchange system 110 may be arranged in a counterflow pathway configuration. That is, the flow pathway is arranged such that cooler, incoming fluid flows in thermal communication with hotter, outgoing fluid. The hotter, outgoing fluid transfers thermal energy to the colder, incoming fluid to assist the heaters in heating the incoming fluid to the pasteurization temperature. This internal preheating of the incoming fluid to a temperature higher than its temperature at the inlet 205 reduces the amount of energy used by the heaters 220 to reach the desired peak temperature. In addition, the transfer of thermal energy from the outgoing fluid to the incoming fluid causes the previously heated, outgoing fluid to cool prior to exiting through the fluid outlet. Thus, the fluid is "cold" as it enters the microfluidic heat exchange system 110, is then heated (first via heat exchange and then via the heaters) as it passes through the internal fluid pathway, and is "cold" once again as it exits the microfluidic heat exchange system 110. In other words, the fluid enters the microfluidic heat exchange system 110 at a first temperature and is heated (via heat exchange and via the heaters) to a second temperature that is greater than the first temperature. As the fluid follows an exit pathway, the fluid (at the second temperature) transfers heat to incoming fluid such that the fluid drops to a third temperature that is lower than the second temperature and that is higher than the first temperature.

Exemplary embodiments of a fluid pathway and corresponding components of the microfluidic heat exchange system 110 are now described in more detail with reference to FIG. 2, which depicts a bayonet-style heat exchanger, with the inlet and outlet on one side of the device, a central heat exchange portion, and a heating section toward the opposite end. The fluid enters the microfluidic heat exchange system 110 through an inlet 205. In the illustrated embodiment, the flow pathway branches into one or more inflow microchannels 210 that are positioned in a counterflow arrangement with an outflow microchannel 215. As mentioned, microfluidic heat exchange system 110 may be formed by a stack of layered lamina. The inflow microchannels 210 may be positioned in separate layers with respect to the outflow microchannels 215 such that inflow microchannels 210 are positioned above or below the outflow microchannels 215 in an interleaved fashion. In another embodiment, the inflow microchannels 210 and outflow microchannels 215 are positioned on a single layer.

The outflow microchannel 215 communicates with an outlet 207. In the illustrated embodiment, the inlet 205 and outlet 207 are positioned on the same end of the microfluidic heat exchange system 110, although the inlet 205 and outlet 207 may also be positioned at different positions relative to one another.

The counterflow arrangement places the inflow microchannels 210 in thermal communication with the outflow microchannel 215. In this regard, fluid in the inflow microchannels 210 may flow along a directional vector that is oriented about 180 degrees to a directional vector of fluid flow in the outflow microchannels 215. The inflow and outflow microchannels may also be in a cross flow configuration wherein fluid in the inflow microchannels 210 may flow along a directional vector that is oriented between about 180 degrees to about 90 degrees relative to a directional vector of fluid flow in the outflow microchannels 215. The orientation of the inflow microchannels relative to the outflow microchannels may vary in any matter that is configured to achieve the desired degree of thermal communication between the inflow and outflow microchannels.

One or more heaters 220 are positioned in thermal communication with at least the inflow microchannels 210 such that the heaters 220 can provide heat to fluid flowing in the system. The heaters 220 may be positioned inside the inflow microchannels 210 such that fluid must flow around multiple sides of the heaters 220. Or, the heaters 220 may be positioned to the side of the inflow microchannels 210 such that fluid flows along one side of the heaters 220. In any event, the heaters 220 transfer heat to the fluid sufficient to cause the temperature of the fluid to achieve a desired temperature, which may include a pasteurization temperature in the case of water to be purified. In an embodiment, the fluid is water and the heaters 220 assist in heating the fluid to a temperature of at least 100 degrees Celsius at standard atmospheric pressure. In an embodiment, the fluid is water and the heaters 220 assist in heating the fluid to a temperature of at least 120 degrees Celsius. In an embodiment, the fluid is water and the heaters 220 assist in heating the fluid to a temperature of at least 130 degrees Celsius. In an embodiment, the fluid is water and the heaters 220 assist in heating the fluid to a temperature of at least 138 degrees Celsius. In another embodiment, the fluid is water and is heated to a temperature in the range of about 138 degrees Celsius to about 150 degrees Celsius. In another embodiment, the fluid is heated to the highest temperature possible without achieving vaporization of the fluid.

Thus, the microfluidic heat exchange system 110 may maintain the fluid as a single phase liquid. Because water typically changes phases from a liquid into a gaseous state around 100 degrees Celsius, heating water to the temperatures set forth above requires pressurization of the heat exchange system so that the single-phase liquid is maintained throughout. Pressures above the saturation pressure corresponding to the highest temperature in the heat exchange system are sufficient to maintain the fluid in a liquid state. As a margin of safety, the pressure is typically kept at 10 psi or higher above the saturation pressure. In an embodiment, the pressure of water in the microfluidic heat exchange system is maintained greater than 485 kPa to prevent boiling of the water, and may be maintained significantly in excess of that level, such as 620 kPa or even as high as 900 kPa, in order to ensure no boiling occurs. These pressures are maintained in the heat exchange system using a pump and a throttling valve. A pump upstream of the heat exchange system and a throttling valve downstream of the heat exchange system are used where the pump and throttling valve operate in a closed loop control setup (such as with sensors) to maintain the desired pressure and flow rate throughout the heat exchange system.

Once the fluid has been heated to the pasteurization temperature, the fluid passes into a residence chamber 225 where the fluid remains heated at or above the pasteurization temperature for a predetermined amount of time, referred to as the "residence time", or sometimes referred to as the "dwell time". In an embodiment, the dwell time can be less than or equal to one second, between one and two seconds, or at least about two seconds depending on the flow path length and flow rate of the fluid. Higher temperatures are more effective at killing bacteria and shorter residence times mean a more compact device. Ultrahigh temperature pasteurization, that is designed to kill all Colony Forming Units (CFUs) of bacteria down to a concentration of less than $10^{-6}$ CFU/ml (such as for purifying the water for use with infusible dialysate is defined to be achieved when water is heated to a temperature of 138 degrees Celsius to 150 degrees Celsius for a dwell time of at least about two seconds. Ultrapure dialysate has a bacterial load no greater than 0.1 CFU/ml. FIG. 14 indicates the required temperature and residence time to achieve various levels of pasteurization. The heat exchange system described herein is configured to achieve the various levels of pasteurization shown in FIG. 14.

The fluid then flows from the residence chamber 225 to the outflow microchannel 215, where it flows toward the fluid outlet 207. As mentioned, the outflow microchannel 215 is positioned in a counterflow relationship with the inflow microchannel 210 and in thermal communication with the inflow microchannel 210. In this manner, outgoing fluid (flowing through the outflow microchannel 215) thermally communicates with the incoming fluid (flowing through the inflow microchannel 210). As the heated fluid flows through the outflow microchannel 215, thermal energy from the heated fluid transfers to the cooler fluid flowing through the adjacent inflow microchannel 210. The exchange of thermal energy results in cooling of the fluid from its residence chamber temperature as it flows through the outflow microchannel 215. Moreover, the incoming fluid is preheated via the heat exchange as it flows through the inflow microchannel 210 prior to reaching the heaters 220. In an embodiment, the fluid in the outgoing microchannel 210 is cooled to a temperature that is no lower than the lowest possible temperature that precludes bacterial infestation of the fluid. When the heat exchange system pasteurizes the fluid, bacteria in the fluid down to the desired level of purification are dead as the fluid exits the heat exchange system. In such a case, the temperature of the fluid after exiting the heat exchange system may be maintained at room temperature before use in dialysis. In another embodiment, the fluid exiting the heat exchange system is cooled to a temperature at or below normal body temperature.

Although an embodiment is shown in FIG. 2 as having an outlet channel sandwiched between an inflow channel, other arrangements of the channels are possible to achieve the desired degrees of heating and cooling and energy requirements of the heaters. Common to all embodiments, however, is that all fluid pathways within the system are designed to be traveled by a single fluid, without the need for a second fluid to add heat to or remove heat from the single fluid. In other words, the single fluid relies on itself, at various positions in the fluid pathway, to heat and cool itself.

The dimensions of the microfluidic heat exchange system 110 may vary. In an embodiment, the microfluidic heat exchange system 110 is sufficiently small to be held in the hand of a user. In another embodiment, the microfluidic heat exchange system 110 is a single body that weighs less than 5 pounds when dry. In another embodiment, the microfluidic heat exchange portion 350 of the overall system 110 has a volume of about one cubic inch. The dimensions of the microfluidic heat exchange system 110 may be selected to achieve desired temperature and dwell time characteristics.

As mentioned, an embodiment of the microfluidic heat exchange system 110 is made up of multiple laminar units stacked atop one another to form layers of laminae. A desired microfluidic fluid flow path may be etched into the surface of each lamina such that, when the laminae are stacked atop one another, microfluidic channels or flow fields are formed between the lamina. Furthermore, both blind etching and through etching may be used for forming the channels in the laminae. In particular, through etching allows the fluid to change the plane of laminae and move to other layers of the stack of laminae. This occurs in one embodiment at the outlet of the inflow laminae where the fluid enters the heater section, as described below. Through etching allows all laminae around the heater section to participate in heating of the fluid instead of maintaining the fluid only in the plane of the inlet laminae. This embodiment provides more surface area and lower overall fluid velocity to facilitate the heating of the fluid to the required temperature and ultimately contributes to the efficiency of the device.

Figure 3A:
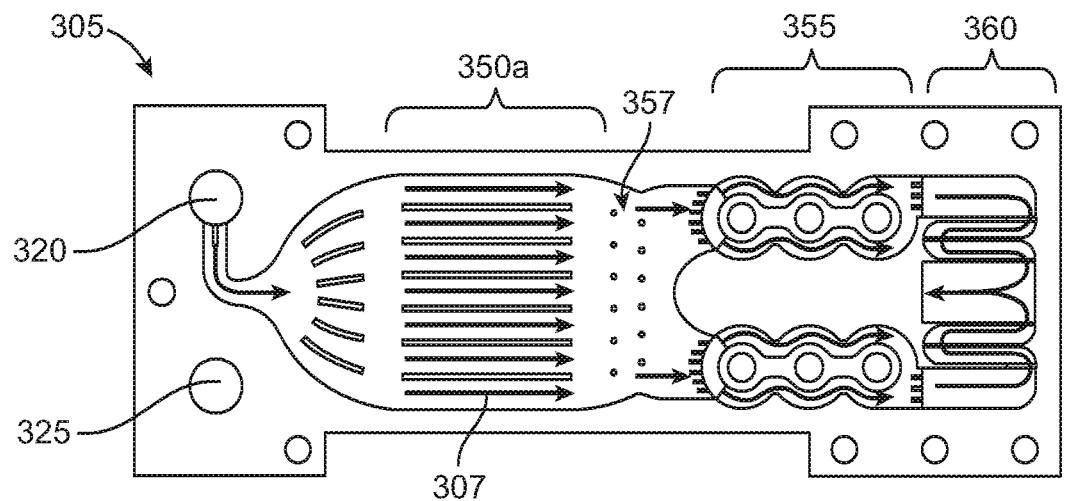
FIG. 3A shows an exemplary embodiment of an inlet lamina that forms at least one inlet pathway where fluid flows in an inward direction through the heat exchange system.
Figure 3B:
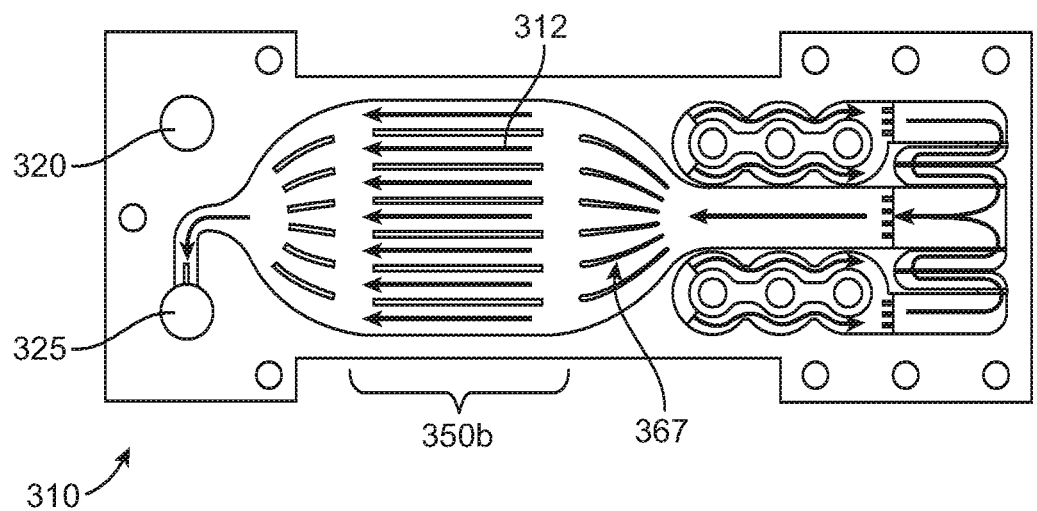
FIG. 3B shows an exemplary embodiment of an outlet lamina that forms at least one outlet pathway where fluid flows in an outward direction through the heat exchange system.

The microchannels or flow fields derived from blind and/or through etching of the laminae form the fluid flow pathways. FIG. 3A shows a plan view of an exemplary embodiment of an inlet lamina 305 that forms at least one inlet pathway where fluid flows in an inward direction (as represented by arrows 307) through the heat exchange system 110. FIG. 3B shows a plan view an exemplary embodiment of an outlet lamina 310 that forms at least one outlet pathway where fluid flows in an outward direction (as represented by arrows 312) through the heat exchange system 110. The inlet pathway and the outlet pathway may each comprise one or more microchannels. In an embodiment, the inlet and outlet pathway comprise a plurality of microchannels arranged in parallel relationship.

Figure 3C:
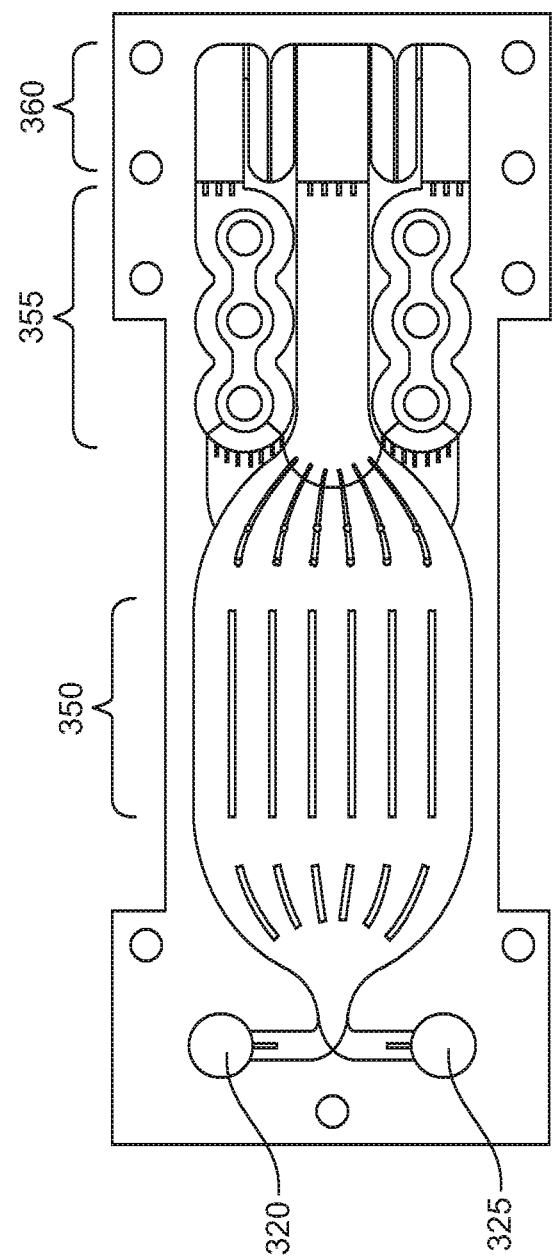
FIG. 3C shows an exemplary embodiment having superimposed inlet and outlet laminae.

FIGS. 3A and 3B show the lamina 305 and 310 positioned adjacent each other, although in assembled device the lamina are stacked atop one another in an interleaved configuration. FIG. 3C shows the inlet lamina 305 and outlet lamina 310 superimposed over one another showing both the inlet pathway and outlet pathway. The inlet lamina 305 and outlet lamina 310 are stacked atop one another with a fluid conduit therebetween so fluid may flow through the conduit from the inlet pathway to the outlet pathway, as described more fully below. When stacked, a transfer layer may be interposed between the inlet lamina 305 and the outlet lamina 310. The transfer layer is configured to permit heat to transfer from fluid in the outlet pathway to fluid in the inlet pathway. The transfer layer may be any material capable of conducting heat from one fluid to another fluid at a sufficient rate for the desired application. Relevant factors include, without limitation, the thermal conductivity of the heat transfer layer 110, the thickness of the heat transfer layer, and the desired rate of heat transfer. Suitable materials include, without limitation, metal, metal alloy, ceramic, polymer, or composites thereof. Suitable metals include, without limitation, stainless steel, iron, copper, aluminum, nickel, titanium, gold, silver, or tin, and alloys of these metals. Copper may be a particularly desirable material. In another embodiment, there is no transfer layer between the inlet and outlet laminae and the laminae themselves serve as the thermal transfer layer between the flow pathways.

The inlet lamina 305 and outlet lamina 310 both include at least one inlet opening 320 and at least one outlet opening 325. When the inlet lamina 305 and outlet lamina 310 are stacked atop one another and properly aligned, the inlet openings 320 align to collectively form a fluid pathway that extends through the stack and communicates with the inlet pathway of the inlet laminae 305, as shown in FIG. 3C. Likewise, the outlet openings 325 also align to collectively form a fluid pathway that communicates with the outlet pathway of the outlet laminae 310. Any quantity of inlet lamina and outlet lamina can be stacked to form multiple layers of inlet and outlet pathways for the heat exchange system 110. The quantity of layers can be selected to provide predetermined characteristics to the microfluidic heat exchange system 110, such as to vary the amount of heat exchange in the fluid, the flow rate of the fluid capable of being handled by the system, etc. In an embodiment, the heat exchange system 110 achieves incoming liquid flow rates of at least 100 ml/min.

In another embodiment, the heat exchange system 110 achieves incoming liquid flow rates of at least 1000 ml/min. Such a heat exchange system may be manufactured of a plurality of laminae in which the microfluidic pathways have been formed using a masking/chemical etching process. The laminae are then diffusion bonded in a stack, as described in more detail below. In an embodiment, the stack includes 40-50 laminae with a flow rate of 2-3 ml/min occurring over each lamina. Higher flow rates can be achieved by increasing the number of pairs of stacked laminae within the heat exchanger. In other embodiments, much higher flow rates can be handled through the system.

In operation, fluid flows into the inlet pathway of the inlet lamina 305 via the inlet opening 320. This is described in more detail with reference to FIG. 4, which shows an enlarged view of an inlet region of the inlet lamina 305. The inlet opening 320 communicates with an inlet conduit 405 that guides the fluid to the inlet pathway. The inlet opening 320 may configured with a predetermined size relative to the size of the inlet conduit 405, which may have a diameter of 2-mm. For example, in an embodiment, the inlet opening 320 has an associated hydraulic diameter that may be about ten to fifteen times larger than the hydraulic diameter of the inlet conduit 405. Such a ratio of hydraulic diameters has been found to force fluid to distribute relatively evenly among the multiple inlet laminae. In another embodiment, for a 2-mm wide inlet flow path, a hydraulic diameter ratio of greater than 10:1, such as 15:1, may be used to ensure an even distribution of fluid flow over the stack.

Figure 4:
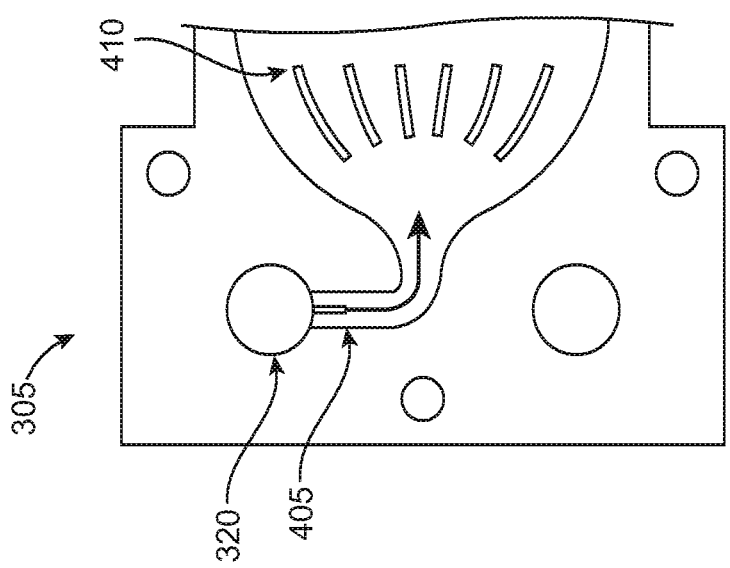
FIG. 4 shows an enlarged view of an inlet region of the inlet lamina.

With reference still to FIG. 4, a downstream end of the inlet conduit 405 opens into the inlet pathway, which flares outward in size relative to the size of the inlet conduit 405. In this regard, one or more flow separation guides, such as fins 410, may be positioned at the entryway to the inlet pathway. The flow separation fins are sized and shaped to encourage an even distribution of fluid as the fluid flows into the inlet pathway from the inlet conduit 405. It should be appreciated that the size, shape, and contour of the inlet conduit 405 and inlet pathway may vary and that the embodiment shown in FIG. 4 is merely exemplary. By way of example only, this region of the system could also comprise a flow field of pin-shaped members (of the sort disclosed in U.S. Provisional Patent Application No. 61/220,117, filed on Jun. 24, 2009, and its corresponding utility application entitled "Microfluidic Devices", filed Jun. 7, 2010, and naming Richard B. Peterson, James R. Curtis, Hailei Wang, Robbie Ingram-Gobel, Luke W. Fisher and Anna E. Garrison, incorporated herein by reference) around which the fluid flows.

With reference again to FIG. 3A, the inlet pathway and outlet pathway each include a heat exchange region. The heat exchange regions are referred to collectively using the reference numeral 350 and individually using reference numeral 350a (for the inlet pathway) and reference numeral 350b (for the outlet pathway). The heat exchange regions 350 are the locations where the colder fluid (relative to the fluid in the outlet pathway) of the inlet pathway receives heat transferred from the hotter fluid (relative to the fluid in the inlet pathway) of the outlet pathway. As discussed above, the relatively colder fluid in the inflow pathway is positioned to flow in thermal communication with the relatively hotter fluid in the outflow pathway. In this layered embodiment, the inflow pathway is positioned immediately above (or below) the outflow pathway when the lamina are stacked. Heat transfers across the transfer layer from the fluid in the outflow pathway to the fluid in the inflow pathway as a result of the temperature differential between the fluid in the inflow pathway and the fluid in the outflow pathway and the thermal conductivity of the material separating the two pathways. Again rather than comprising a series of microchannels, the heat exchange regions may also comprise a microfluidic flow field as described above.

Figure 5:
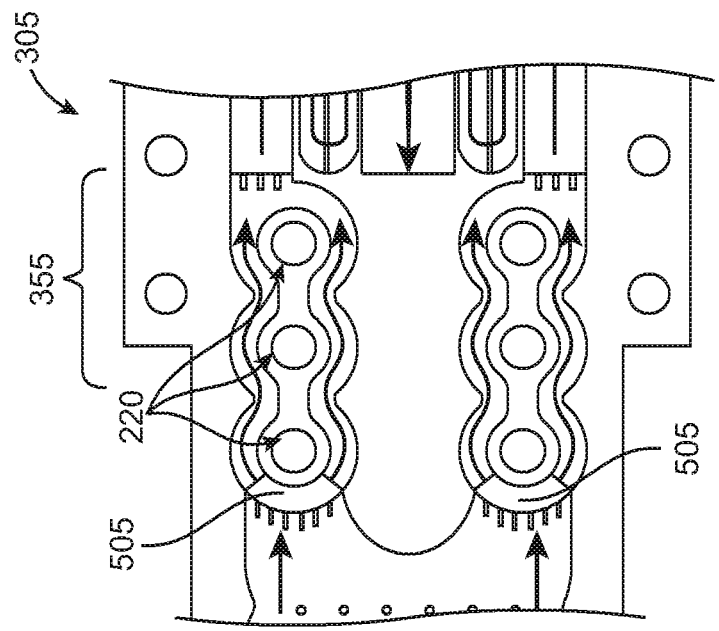
FIG. 5 shows an enlarged view of a heater region of the inlet lamina.

With reference still to FIG. 3A, the fluid in the inflow pathway flows into a heater region 355 from the heat exchange region 350. A plurality of pins 357 may be positioned in the inlet flow pathway between the heat exchange region 350 and the heater region 355. The pins 357 disrupt the fluid flow and promote mixing, which may improve both fluid flow and heat distribution. FIG. 5 shows an enlarged view of the heater region 355. In an embodiment, the inflow pathway bifurcates into at least two flow pathways in the heater region 355 to accommodate a desired flow rate. Alternatively only one flow path through the heater region may be utilized, or three or more flow paths may be selected. The heater region 355 includes one or more heaters 220 that thermally communicate with fluid flowing through this region, but are hermetically isolated from the flow path. The heaters 220 add heat to the incoming fluid sufficient to raise temperature of the fluid to the desired temperature, which may include a pasteurization temperature. The incoming fluid was previously preheated as it flowed through the heat exchange region 350. This advantageously reduced the energy requirements for the heaters.

The laminae in the stack may include through-etches at entry locations 505 to the heater region 355 such that fluid entering the heater region can pass through all the laminae in the stack. Through etching allows all laminae around the heater section to participate in heating of the fluid instead of maintaining the fluid only in the plane of the inlet laminae. This provides more surface area between the fluid and the heaters and also provides lower overall fluid velocity to facilitate the heating of the fluid to the required temperature.

As mentioned, the inflow pathway may bifurcate into multiple flow pathways. Each pathway may include one or more heaters 220 arranged within the pathway so as to maximize or otherwise increase the amount of surface area contact between the heaters 220 and fluid flowing through the pathways. In this regard, the heaters 220 may be positioned towards the middle of the pathway such that the fluid must flow around either side of the heaters 220 along a semicircular or otherwise curvilinear pathway around the heaters 220. The heaters 220 can vary in configuration. In an embodiment, the heaters 220 are conventional cartridge heaters with a ⅛-inch diameter which can be run in an embodiment at a combined rate of between about 70,000 and 110,000 W/m2, which results in energy usages of less than 100 W in one embodiment, and less than 200 W in another embodiment, for the entire stack running at about 100 mL/minute. In an embodiment, the system uses six heaters in a configuration of three heaters per flow pathway wherein each heater uses about 70 W for a 100 ml/min flow rate. In an embodiment the fluid is forced to flow around the heaters in paths 1.6 mm wide.

With reference again to FIG. 3A, the inflow pathway transitions from the heater section 355 to the residence chamber 360. By the time the fluid flows into the residence chamber 360, it has been heated to the desired temperature, such as the pasteurization temperature, as a result of the heat transfer in the heat exchange region 350 and/or by being heated in the heater section 355. In the case of multiple laminae being stacked, the residence chamber 360 may be a single chamber that spans all of the layers of laminae in the stack such that the fluid from each inlet lamina flows into a single volume of fluid in the residence chamber 360. The residence chamber 360 is configured such that fluid flow 'shortcuts' are eliminated, all of the fluid is forced to travel a flow pathway such that no portion of the fluid will reside in the residence chamber for the less than the desired duration at a specified flow rate, and the fluid is maintained at or above the pasteurization temperature for the duration of the time (i.e., the dwell time) that the fluid is within the residence chamber 360. In effect, the residence time is a result of the dimensions of the flowpath through the residence area and the flow rate. It will thus be apparent to one of skill in the art how to design a residence pathway for a desired duration.

Figure 6:
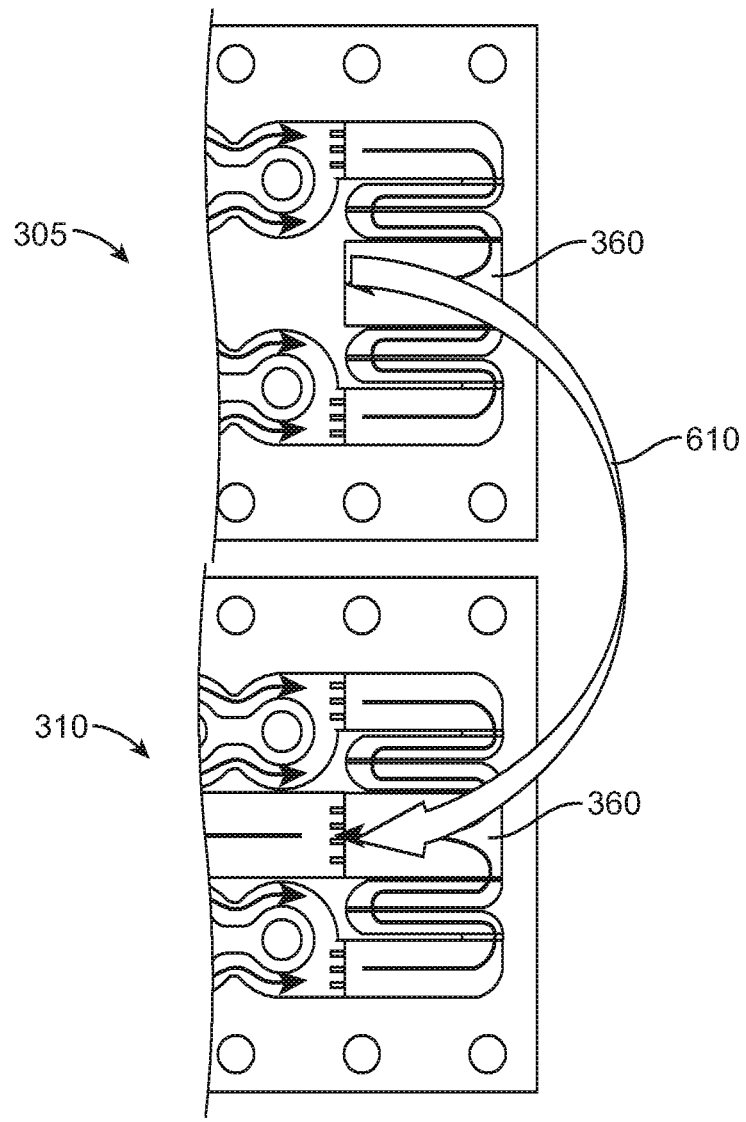
FIG. 6 shows an enlarged view of a residence chamber of both the inlet lamina and outlet lamina.

FIG. 6 shows an enlarged view of the region of the residence chamber 360 for the inlet lamina 305 and outlet lamina 310. For clarity of illustration, FIG. 6 shows the inlet lamina 305 and outlet lamina 310 positioned side-by-side although in use the laminae are stacked atop one another such that the residence chambers align to form a residence chamber that spans upward along the stack. In an embodiment, the residence chamber 360 incorporates a serpentine flow path as shown in the enlarged view of the residence chamber of FIG. 6. The serpentine flow path provides a longer flow path to increase the likelihood of the liquid spending a sufficient amount of time within the residence chamber 360.

After the fluid has reached the end of the serpentine flow path, it passes (represented by arrow 610 in FIG. 6) to the outlet pathway of the outlet lamina 310. With reference now to FIG. 3B, the outlet pathway passes between the heaters 220, which act as insulators for the fluid to lessen the likelihood of the fluid losing heat at this stage of the flow pathway. The heated fluid of the outlet pathway then flows toward the heat exchange region 350b. The outlet flow pathway expands prior to reaching the heat exchange region 350b. A set of expansion fans 367 directs the fluid into the expanded heat exchange region 350b of the outlet pathway, where the fluid thermally communicates with the cooler fluid in the inflow pathway. As discussed, heat from the fluid in the hotter outflow pathway transfers to the cooler fluid in the inflow pathway. This results in cooling of the outflowing fluid and heating of the inflowing fluid. The fluid then flows from the heat exchange region 350b to the outlet opening 325. At this stage, the fluid is in a cooled, pasteurized state.

In an embodiment, laminae having a thickness of 350 microns with an etch-depth of 175 microns, with 2.5-mm wide channels having a hydraulic diameter of 327 microns were utilized. Each pair of laminae was able to handle a fluid flow rate of approximately 3.3. mL/min of fluid, which thus required 30 pairs of laminae in order to facilitate a flow of 100 mL/min, with only a 15-mm long heat exchanger section. In an embodiment, the fluid flowpaths are designed in smooth, sweeping curves and are substantially symmetrically designed along the longitudinal axis of the stack; if the flow paths are not designed symmetrically, they are designed to minimize differences in the path line or lengths so as to evenly distribute the flow, the heating of the fluid and the various dwell times.

The width of the ribs separating channels in the heat exchange portion can be reduced, which would have the effect of increasing the available heat transfer area and reducing the length of the heat exchange portion required for the desired energy efficiency level of the device. Energy efficiency levels of at least about 85%, and in some embodiment of at least about 90% can be achieved, meaning that 90% of the thermal energy from the outgoing fluid can be transferred to the incoming fluid stream and recaptured without loss.

In this manner, a heat exchange system may be constructed to provide pasteurized water continuously at a desired flow rate for real-time mixing of dialysate in a dialysis system, without the need either to heat, purify and store water in batched quantities or to provide bags of pure water or of premixed dialysate for use by the patient.

FIG. 7A shows a plan view of another embodiment of an inlet lamina 705 that forms at least one inlet pathway where fluid flows in an inward direction (as represented by arrows 707) through the heat exchange system 110. FIG. 7B shows a plan view another embodiment of an outlet lamina 710 that forms at least one outlet pathway where fluid flows in an outward direction (as represented by arrows 712) through the heat exchange system 110. The flow pathway in this embodiment generally follows a different contour than the flow pathway of the embodiment of FIGS. 3A and 3B. In actual use, the inlet lamina 705 and outlet lamina 710 are stacked atop one another.

The fluid enters the inlet pathway of the inlet lamina 705 at an inlet 720. The inlet pathway then splits into multiple pathways at the heat exchange region 750 a, which thermally communicates with a corresponding heat exchange region 750 b of the outlet lamina 710. In another embodiment, the inlet pathway does not split into multiple pathways but remains a single pathway. The inlet pathway could also be at least partially formed of one or more microfluidic flow fields as disclosed in U.S. Provisional Patent Application No. 61/220,117, filed on Jun. 24, 2009, and its corresponding utility application entitled "Microfluidic Devices", filed Jun. 7, 2010, and naming Richard B. Peterson, James R. Curtis, Hailei Wang, Robbie Ingram-Gobel, Luke W. Fisher and Anna E. Garrison, incorporated herein by reference. After the heat exchange region 750 a, the inlet pathway transitions to an arc-shaped heater region 760 that thermally communicates with a heater 765, such as a 150-Watt McMaster-Carr cartridge heater (model 3618K451). The heater region serves as both a region where the heater 765 heats the fluid and as a residence chamber where the fluid remains heated at or above the desired temperature for a predetermined amount of time.

From the heater region 760 and residence chamber of the inlet lamina 710, the fluid flows to the outlet lamina 710 at an entrance location 770. The fluid then flows into the heat exchange region 750b of the outlet lamina 710, where the fluid transfers heat to the incoming fluid flowing through the heat exchange region 750a of the inlet lamina 705. The fluid then exits the outlet lamina at an outlet 775. In embodiment, the lamina 705 and 710 are about 600 µm thick and the microfluidic flow pathways have a depth of about 400 µm to 600 µm. In each of the embodiments disclosed herein, the fluid flow path completely encircles each of the heaters so that any shim material conducting heat away from the heater will have fluid flowing over it to receive the heat, thereby minimizing heat loss to the environment. In addition, ideally, the flowpaths around each heater will be relatively narrow so that non-uniform heating due to separation from the heaters will be avoided.

As mentioned, the microfluidic heat exchange system 110 may be formed of a plurality of lamina stacked atop one another and diffusion bonded. Additional information concerning diffusion bonding is provided by U.S. patent application Ser. Nos. 11/897,998 and 12/238,404, which are incorporated herein by reference. In an embodiment, the stack includes multiple sets of lamina with each set including an inlet lamina 305 juxtaposed with an outlet lamina 310. Each set of juxtaposed inlet lamina and outlet lamina forms a single heat exchange unit. The stack of lamina may therefore include a plurality of heat exchange units wherein each unit is formed of an inlet lamina 305 coupled to an outlet lamina 310. The flow pathways for each lamina may be formed by etching on the surface of the lamina, such as by etching on one side only of each lamina. When the laminae are juxtaposed, the etched side of a lamina seals against the unetched sided of an adjacent, neighboring lamina. This may provide desirable conditions for heat exchange and separation of the incoming fluid (which is not pasteurized) and the outgoing fluid (which is pasteurized).

Figure 8:
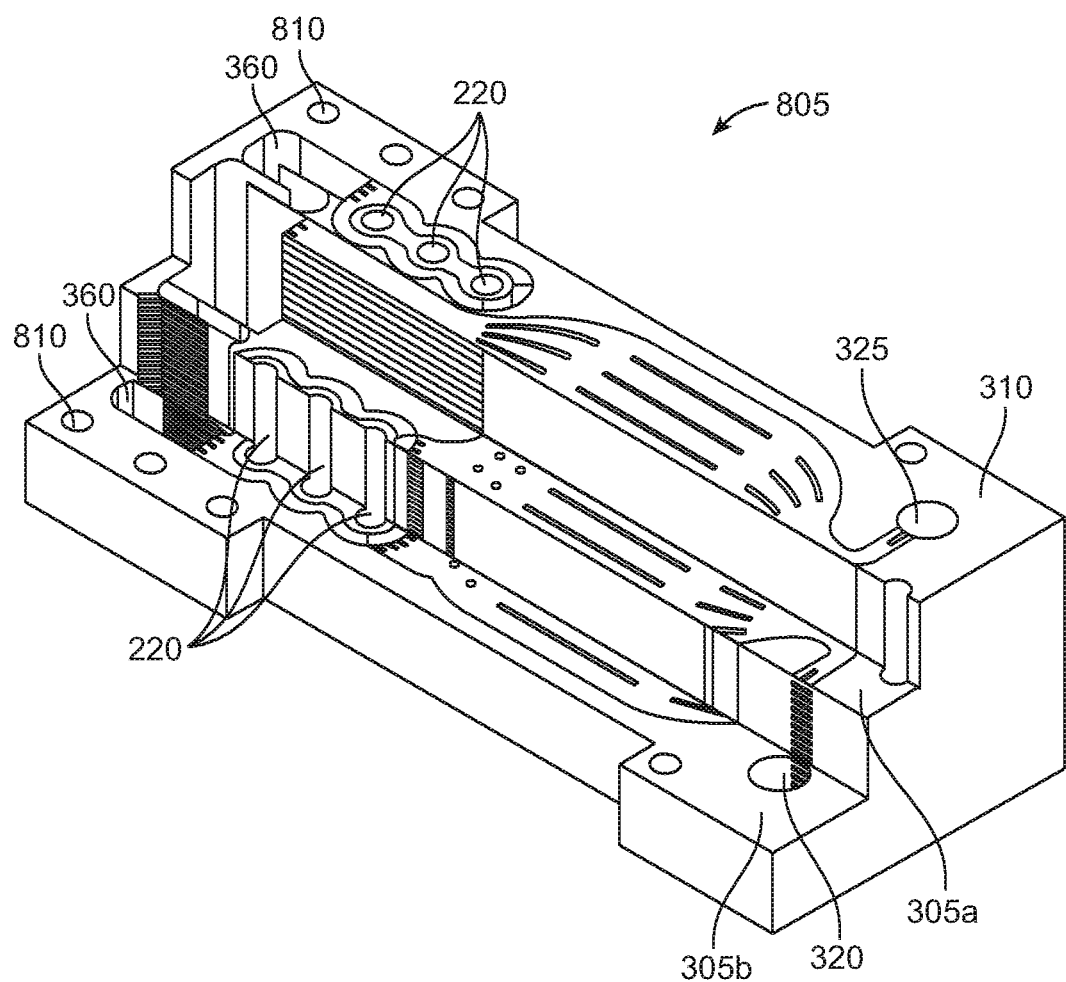
FIG. 8 shows a perspective view of an exemplary stack 805 of laminae.

FIG. 8 shows a perspective view of an exemplary stack 805 of laminae. The stack 805 is shown in partial cross-section at various levels of the stack including at an upper-most outlet lamina 310, a mid-level inlet lamina 305a, and a lower level inlet lamina 305b. As mentioned, the stack 805 is formed of alternating inlet lamina and outlet lamina interleaved with one another. The heaters 220 are positioned within cut-outs that extend through the entire stack 805 across all the laminae in the stack 805. The residence chamber 360 and the aligned inlet openings 320 and outlet openings 325 also extend entirely through the stack 805. The laminae may also include one or more holes 810 that align when the lamina are stacked to form shafts through which alignment posts may be inserted.

The quantity of laminae in the stack may be varied to accommodate desired specifications for the microfluidic heat exchange system 110, such as the heating specifications. The heating specifications may be dependent on flow rate of fluid, heater power input, initial temperature of incoming fluid, etc. In an embodiment, the stack 805 is less than about 100 mm long, less than about 50 mm wide at its widest dimension, and less than about 50 mm deep, with a volume of less than about 250 cubic centimeters, although the dimensions may vary. In another embodiment, the stack 805 is about 82 mm long, about 32 mm wide at its widest dimension, and about 26 mm deep, with a volume of about 69-70 cubic centimeters, and a weight of about five pounds when dry, although the dimensions may vary.

The lamina 305 and 310 may be any material capable of being patterned with features useful for a particular application, such as microchannels. The thickness of the lamina may vary. For example, the lamina may have a thickness in the range of about 200 µm to about 100 µm. In another embodiment, the lamina may have a thickness in the range of about 500 µm to about 100 µm. Some suitable lamina materials include, without limitation, polymers and metals. The lamina may be manufactured of any diffusion bondable metal, including stainless steel, copper, titanium alloy, as well as diffusion bondable plastics. Because of the operating pressures and temperatures involved, the need to avoid leaching of the lamina material into the heated fluid, such as water, and the desirability of multiple uses of this device before disposal, it has been found that manufacturing the heat exchange system from stainless steel, such as 316L stainless steel, has proven adequate, although other materials may be used as long as they withstand the operating conditions without degradation.

The laminae are stacked in a manner that achieves proper alignment of the lamina. For example, when properly stacked, the inlet openings 320 of all the lamina align to collectively form an inlet passage for fluid to flow into the system and the outlet openings 325 align to collectively form an outlet passage, as shown in FIG. 8. The properly-aligned stack of lamina may also include one or more seats for coupling the heaters 220 in the stack. One or more features can be used to assist in proper alignment of the lamina in the stack, such as alignment posts and/or visual indicators of proper alignment. The stack may include a top cover positioned on the top-most lamina and a bottom cover positioned on the bottom-most lamina. The stack may also include an external insulation wrap to prevent heat loss to the outside environment.

Figure 9:
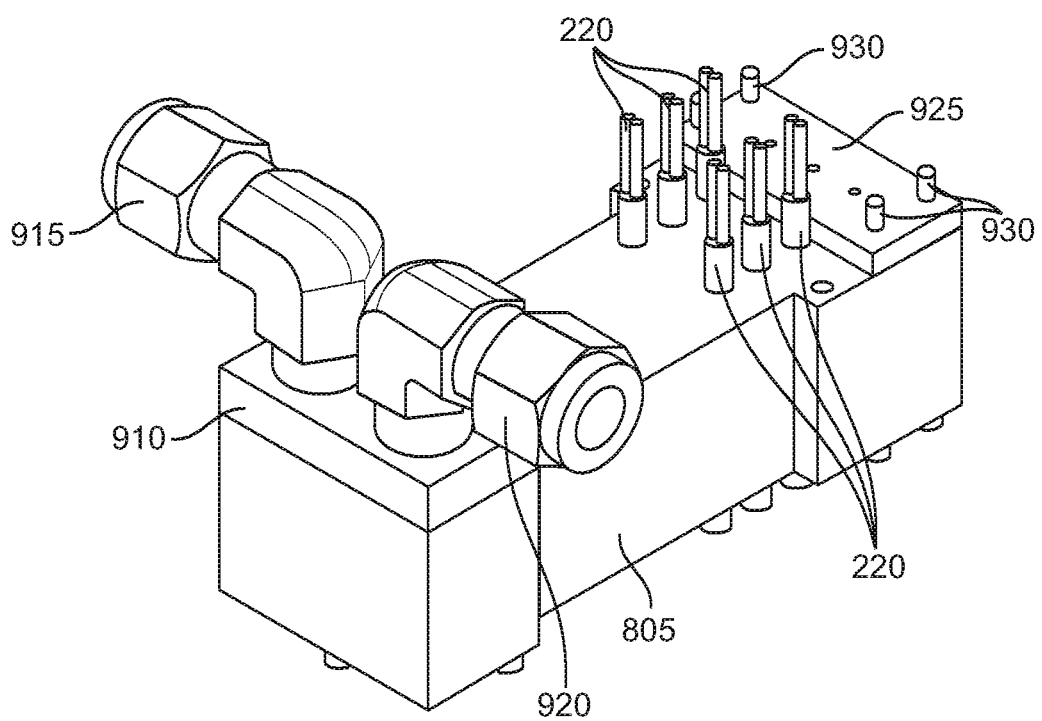
FIG. 9 shows a perspective view of an example of an assembled microfluidic heat exchange system.

FIG. 9 shows a perspective view of an example of an assembled microfluidic heat exchange system 110. The stack 805 of inlet/outlet laminae includes chemically etched upper and lower covers that seal the stack 805 against the atmosphere. These covers typically are thicker than the laminae, and may be about 1 mm or more in thickness in an embodiment to withstand damage and the operating pressures necessary to maintain the fluid in a single state. The cartridge heaters 220 are mounted in cavities that extend through the entire stack 805. A plate 910 is secured (such as via bolts) to the stack and provides a means of securing an inlet port 915 and an outlet port 920 to the stack 805. The inlet port 915 and outlet port 920 can be piping having internal lumens that communicate with the inlet openings 320 and outlet openings 325.

Before assembly of the stack, each hole of each lamina that is to accept a cartridge heater is designed slightly smaller than the diameter of the cartridge heater itself. After assembly of the entire stack, the hole is enlarged for a clearance fit between the hole inner diameter and the cartridge heater outer diameter, taking into account thermal expansion of the heater during operation, to provide a uniform surface for optimum heat transfer from the heater to the pasteurizer. This method avoids any potential issues with misalignment of the shims if the holes in each shim were to be properly sized to the cartridge heater prior to assembly.

A second plate 925 is also secured to the stack 805. The plate 925 is used to couple one or more elongated and sheathed thermocouples 930 to the stack 805. The thermocouples 930 extend through the stack 805 and communicate with the laminae in the stack 805 in the region of the dwell chamber for monitoring fluid temperature in the dwell chamber. The thermocouples that are to be inserted into solid sections of the stack utilize a slip fit for installation. The thermocouples that enter into the fluid flow paths require a seal to prevent fluid leakage. In these cases, the holes for accepting the thermocouples are generated after the stack is assembled by electrical discharge machining (EDM), because this technique generates very small debris that can easily be flushed out of the system, as compared with traditional drilling, which could result in larger debris blocking some of the flow paths. Any of a variety of sealing members, such as o-rings or gaskets, may be coupled to the stack to provide a sealed relationship with components attached to the stack, such as the plates 910 and 925, thermocouples 930, and inlet port 915 and outlet port 920. It should be appreciated that the assembled microfluidic heat exchange system 110 shown in FIG. 9 is an example and that other configurations are possible.

In an exemplary manufacture process, a stack of lamina is positioned in a fixture or casing and is then placed into a bonding machine, such as a high temperature vacuum-press oven or an inert gas furnace. The machine creates a high temperature, high pressure environment that causes the lamina to physically bond to one another.

In an embodiment, the weight of the overall stack can be reduced by removing some of the excess material from the sides of the stack, thereby eliminating the rectangular footprint in favor of a more material-efficient polygonal footprint.

Figure 11:
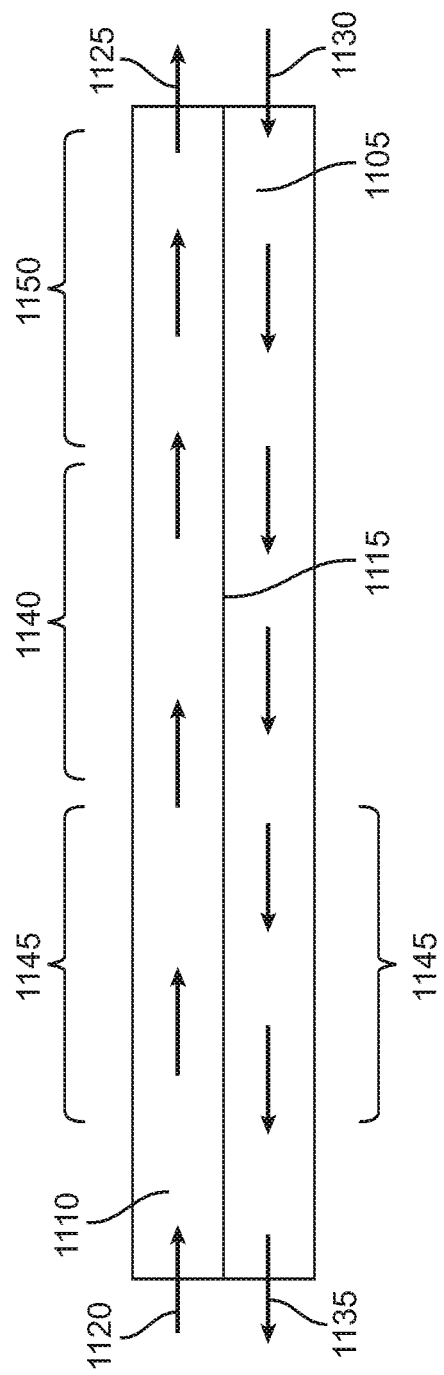
FIG. 11 shows a schematic, plan view of another exemplary embodiment of flow pathways for the microfluidic heat exchange system.

FIG. 11 shows a schematic, plan view of another exemplary embodiment of the microfluidic heat exchange system 110. FIG. 11 is schematic and it should be appreciated that variations in the actual configuration of the flow pathway, such as size and shape of the flow pathway, are possible. The embodiment of FIG. 11 includes a first flow pathway 1105 and a second flow pathway 1110 separated by a transfer layer 1115. Fluid enters the first flow pathway at an inlet 1120 and exits at an outlet 1125. Fluid enters the second flow pathway at an inlet 1130 and exits at an outlet 1135. The first and second flow pathways are arranged in a counterflow configuration such that fluid flows through the first flow pathway 1105 in a first direction and fluid flows through the second flow pathway 1110 in a direction opposite the first direction. In this regard, the inlet 1120 of the first flow pathway 1105 is located on the same side of the device as the outlet 1135 of the second flow pathway 1110. Likewise, the outlet 1125 of the first flow pathway 1105 is located on the same side of the device as the inlet 1130 of the second flow pathway 1110. The flow pathways may be least partially formed of one or more microchannels, although utilizing microfluidic flow fields as disclosed in U.S. Provisional Patent Application No. 61/220,117, filed on Jun. 24, 2009, and its corresponding utility application entitled "Microfluidic Devices", filed Jun. 7, 2010, and naming Richard B. Peterson, James R. Curtis, Hailei Wang, Robbie Ingram-Gobel, Luke W. Fisher and Anna E. Garrison, incorporated herein by reference, for portions of the fluid flow pathway is also within the scope of the invention.

With reference still to FIG. 11, fluid enters the first flow pathway 1120 at the inlet 1120 and passes through a heater region 1140. A heater is positioned in thermal communication with the heater region 1140 so as to input heat into the fluid passing through the heater region 1140. Prior to passing through the heater region 1140, the fluid passes through a heat exchange region 1145 that is in thermal communication (via the transfer layer 1115) with fluid flowing through the second flow pathway 1110. In an embodiment, the fluid flowing through the second flow pathway 1110 is fluid that previously exited the first flow pathway 1105 (via the outlet 1125) and was routed into the inlet 1125 of the second flow pathway 1110. As the previously-heated fluid flows through the second flow pathway 1110, thermal energy from the previously-heated fluid in the second flow pathway 110 transfers to the fluid flowing through the first flow pathway 1120. In this manner, the fluid in the second flow pathway 1110 pre-heats the fluid in the heat exchange region 1145 of the first flow pathway prior to the fluid reaching the heater region 1140.

In the heater region 1140, the heater provides sufficient thermal energy to heat the fluid to a desired temperature, which may be the pasteurization temperature of the fluid. From the heater region 1140, the fluid flows into a residence chamber 1150 where the fluid remains heated at or above the desired temperature for the residence time. The fluid desirably remains flowing, rather than stagnant, while in the residence chamber 1150. From the residence chamber 1150, the fluid exits the first flow pathway 1105 through the outlet 1125 and is routed into the inlet 1130 of the second flow pathway 1110.

The fluid then flows through the second flow pathway 1110 toward the outlet 1135. As mentioned, the second flow pathway 1110 is in thermal communication with the first flow pathway 1105 at least at the heat exchange region 1145. In this manner, the previously-heated fluid flowing through the second flow pathway 1110 thermally communicates with the fluid flowing through the first flow pathway 1105. As the previously-heated fluid flows through the second flow pathway 1110, thermal energy from the heated fluid transfers to the fluid flowing through the adjacent heat exchange region 1145 of the first flow pathway 1105. The exchange of thermal energy results in cooling of the fluid from its residence chamber temperature as it flows through the second flow pathway 1110. In an embodiment, the fluid in the second flow pathway 1110 is cooled to a temperature that is no lower than the lowest possible temperature that precludes bacterial infestation of the fluid.

In another embodiment of the device of FIG. 11, the fluid flowing into the second flow pathway 1110 is not fluid re-routed from the first flow pathway 1105 but is rather a separate fluid flow from the same source as, or from a different source than, the source for the first fluid flow pathway 1105. The fluid in the second flow pathway 1110 may or may not be the same type of fluid in the first flow pathway 1105. For example, water may flow through both pathways; or water may flow through one flow pathway and a non-water fluid may flow through the other flow pathway. In this embodiment where a separate fluid flows through the second pathway relative to the first pathway, the separate fluid has desirably been pre-heated in order to be able to transfer heat to the fluid in the first flow pathway 1105 at the heat exchange region 1145.

As in the previous embodiments, the embodiment of FIG. 11 may be made up of multiple laminar units stacked atop one another to form layers of laminae. In addition, the embodiment of FIG. 11 may have the same or similar specifications as the other embodiments described herein, including materials, dimensions, residence times, and temperature levels.

Figure 12:
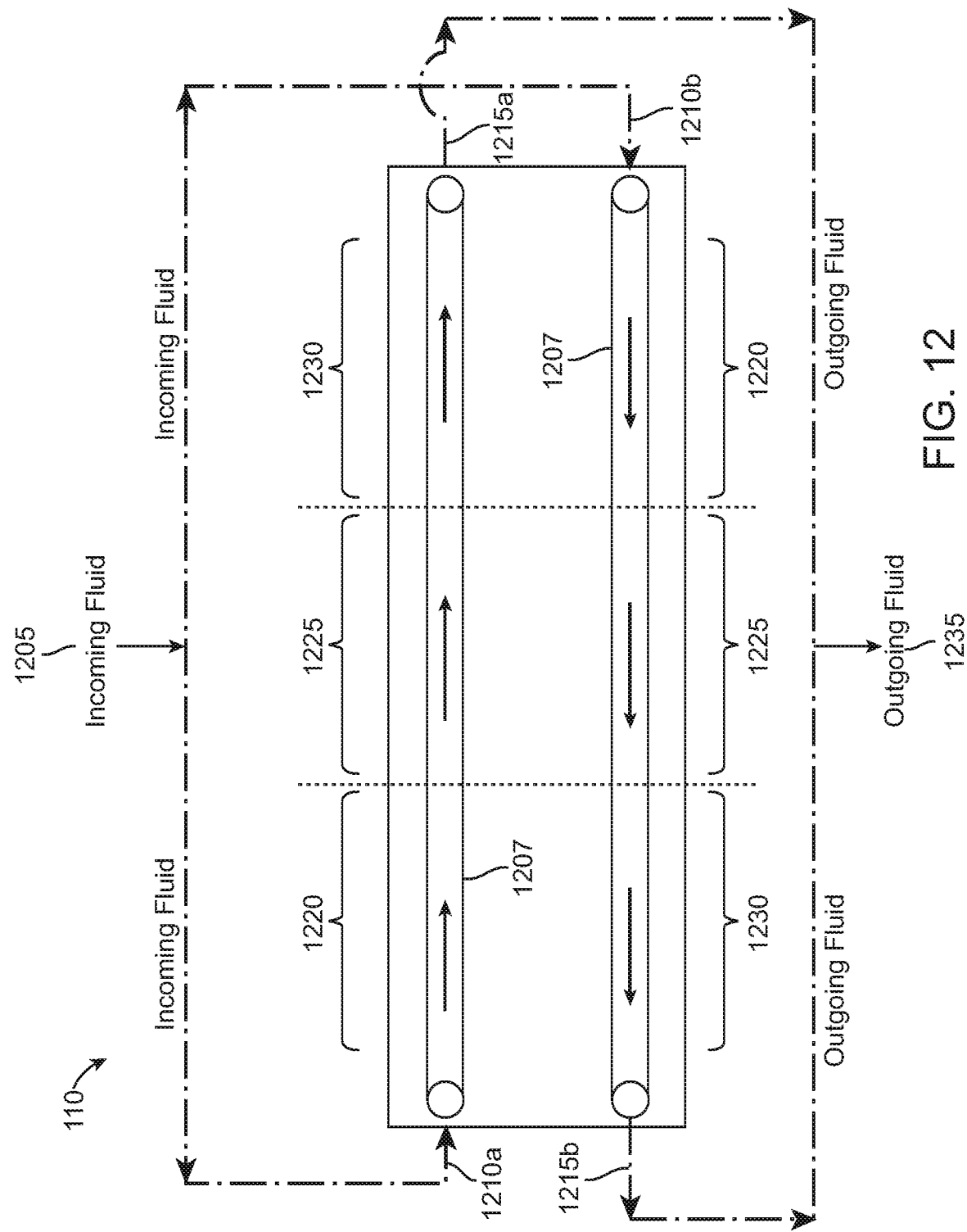
FIG. 12 shows a schematic, plan view of another exemplary embodiment of flow pathways for the microfluidic heat exchange system.

In another embodiment shown in FIG. 12, a microfluidic heat exchange system 110 purifies a single fluid. FIG. 12 represents an exemplary flow pathway configuration for a single lamina. A plurality of such laminae may be interleaved to form a stack of lamina as described above for other embodiments. The purification of the fluid may comprise pasteurizing the fluid although pasteurization is not necessary such as where the device is not used for dialysis. The heat exchange system receives a stream of incoming fluid 1205, which splits before entering the heat exchange system. A first portion of the stream of incoming fluid 1205a enters at a first inlet 1210a on one end of the system and a second portion of the stream of incoming fluid 1205 enters at a second inlet 1205b on the other, opposite end of the system. The two streams of incoming fluid 1205 are distributed across the stacked laminae in alternating fashion such that there is no direct contact between the two fluid streams.

Each stream of incoming fluid 1205 enters a flow pathway 1207 and flows along the flow pathway toward an outlet 1215. One stream of fluid enters via the inlet 1205a and exits at an outlet 1215a positioned on the same end of the system as the inlet 1210b, while the other stream of fluid enters via the inlet 1205b and exits at an outlet 1215b on the same end of the system as the inlet 1210a. Each flow pathway 1207 includes a first heat exchange region 1220 where heat is exchanged through a transfer layer between the incoming fluid and the previously-heated outgoing fluid flowing through a lamina immediately above (or below) the instant lamina in the stack. As the fluid flows through the heat exchange region 1220 it receives heat via the heat transfer and is pre-heated prior to entering a heater region 1225.

For each flow pathway 1207, the fluid then flows into the heater region 1225, which thermally communicates with at least one heater, and preferably multiple heaters, for communicating heat into the flowing fluid. The fluid is heated under pressure to a temperature at or above the desired threshold pasteurization temperature as described above for other embodiments. The heater region 1225 also serves as a residence chamber. The fluid flows through the residence chamber while held at or above the desired temperature for the desired residence time. The desired residence time may be achieved, for example, by varying the flow rate and/or by employing a serpentine flow path of the required length within the heater region 1225. After leaving the heater region 1225, the outgoing fluid enters a second heat exchange region 1230 where the outgoing fluid exchanges heat with the incoming fluid flowing through a lamina immediately above (or below) the instant lamina in the stack. The outgoing fluid then exits the flow pathways through the outlets 1210a and 1210b. The two streams of outgoing fluid then recombine into a single stream of outgoing fluid 1235 before continuing on to the ultrafilter to remove all or substantially all of the dead bacteria killed by the pasteurization process.

Figure 13B:
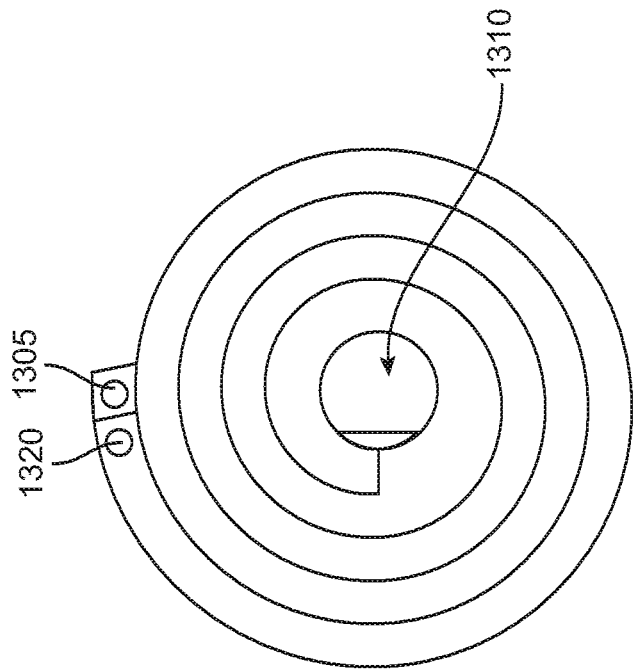
FIG. 13B shows another embodiment of an outlet lamina that forms an outlet pathway where fluid flows in an outward direction through the heat exchange system.
Figure 13A:
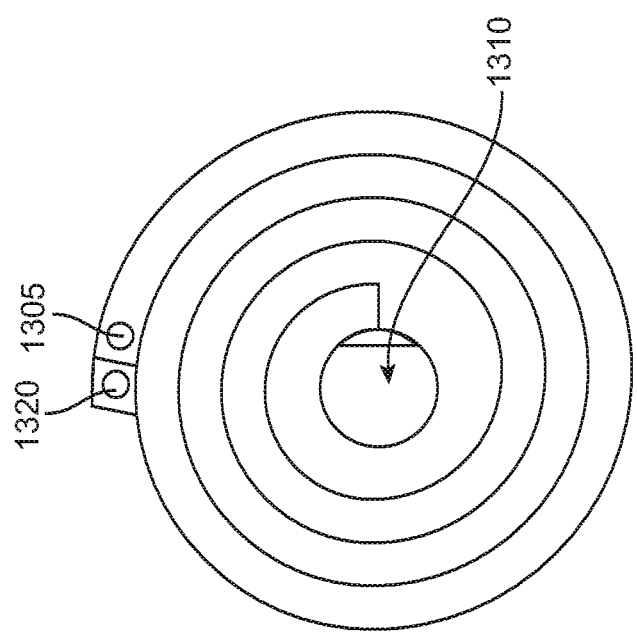
FIG. 13A shows another embodiment of an inlet lamina that forms an inlet pathway where fluid flows in an inward direction through the heat exchange system.

FIG. 13A shows another embodiment of an inlet lamina that forms a spiral inlet pathway where fluid flows in an inward direction through the heat exchange system. FIG. 13B shows a corresponding outlet lamina that forms a similar spiral pathway where fluid flows in an outward direction. A plurality of such inlet and outlet laminae may be interleaved to form a stack of laminae as described above for other embodiments. The laminae are shown having a circular outer contour although the outer shape may vary as with the other embodiments.

With reference to FIG. 13A, the inlet lamina has a header forming an inlet 1305 where incoming fluid enters the inlet pathway. The inlet pathway spirals inward toward a center of the pathway, where a heating chamber 1310 is located. The heating chamber 1310 also serves as a residence chamber for the fluid, as described below. One or more heaters are positioned in thermal communication with the heating chamber 1310 to provide heat to fluid flowing in the heating chamber 1310. The heating chamber 1310 extends across multiple laminae in the stack and includes a conduit that communicates with the outlet lamina shown in FIG. 13B. The fluid enters the outlet lamina from the heating chamber 1310. The outlet lamina has an outflow pathway that spirals outward from the heating chamber 1310 toward an outlet 1320.

In use, the fluid enters the inlet pathway of the inlet lamina through the inlet 1305 shown in FIG. 13B. The fluid then flows along the spiral inlet pathway toward the heater chamber 1310. As in the previous embodiments, the incoming fluid is at a temperature that is less than the previously-heated fluid flowing through the outlet lamina, which is positioned immediately above or below the inlet lamina. As the fluid flows through the inlet pathway, the fluid receives heat from the previously-heated fluid flowing through the outlet pathway of the outlet lamina. This serves to pre-heat the fluid prior to the fluid flowing into the heating chamber 1310. The fluid then flows into the heating chamber 1310 where the fluid receives heat from the one or more heaters.

While in the heating chamber 1310, the fluid is heated under pressure to a temperature at or above the desired threshold pasteurization temperature as described above for other embodiments. As mentioned, the heating chamber 1310 also serves as a residence chamber. The fluid flows through the residence chamber while held at or above the desired temperature for the desired residence time. As in other embodiments, the desired residence time may be achieved, for example, by varying the flow rate and/or by employing a serpentine flow path of the required length within the heater chamber 1310. After leaving the heater chamber, the outgoing fluid enters the outlet pathway of an outlet lamina such as shown in FIG. 13B. The outgoing fluid flows outward from the heating chamber 1310 along the spiral flow pathway toward the outlet 1320. The spiral pathway of the inlet lamina thermally communicates with the spiral pathway of the outlet lamina across a transfer layer As the outgoing fluid flows along the spiral pathway, it exchanges heat with the incoming fluid flowing through an inlet lamina immediately above (or below) the instant lamina in the stack. The outgoing fluid then exits the stack of lamina via the outlet 1320 before continuing on to the ultrafilter to remove all or substantially all of the dead bacteria killed by the pasteurization process.

Control System

Figure 10:
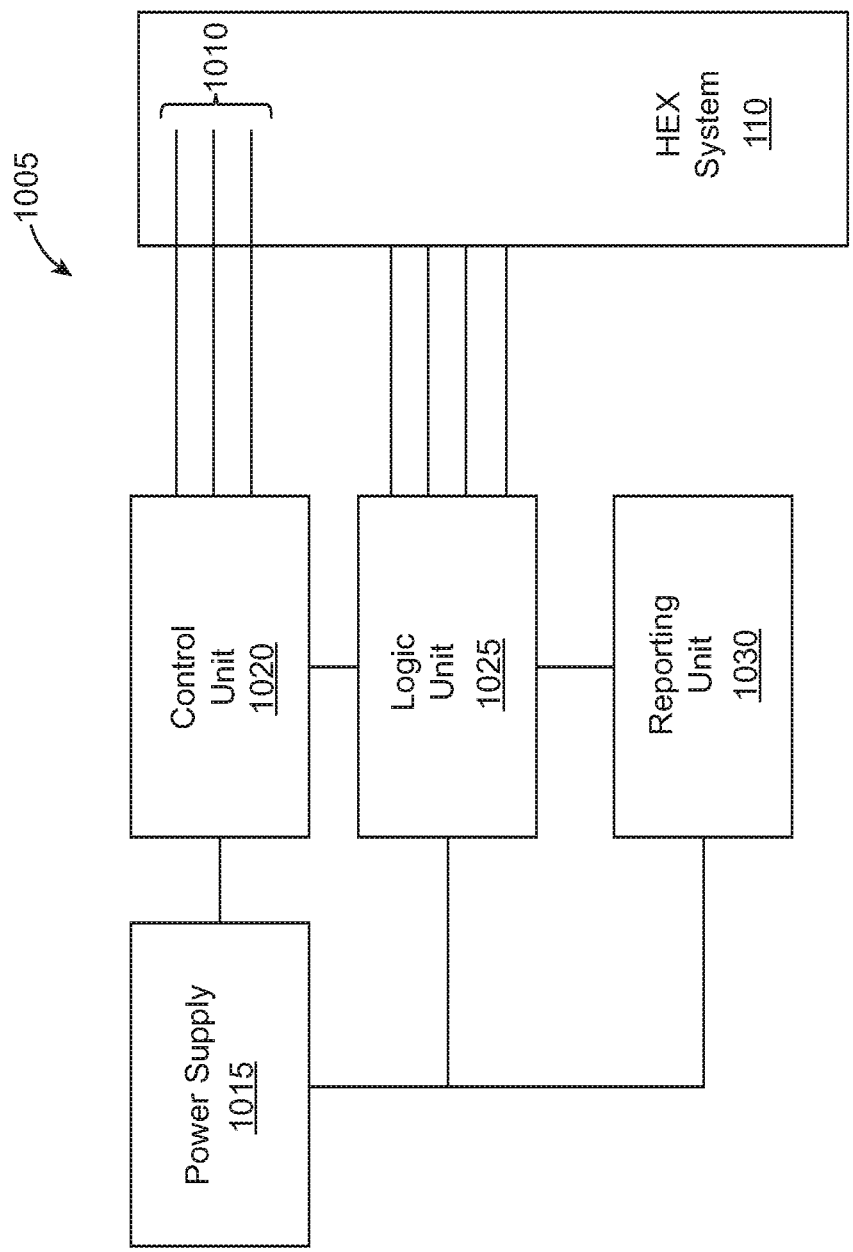
FIG. 10 shows a schematic view of an exemplary heater control system coupled to the microfluidic heat exchange system.

The microfluidic heat exchange system 110 may include or may be coupled to a control system adapted to regulate and/or control one or more aspects of the fluid flow through the system, such as fluid flow rate, temperature and/or pressure of the fluid, chemical concentration of the fluid, etc. FIG. 10 shows a schematic view of an exemplary heater control system 805 communicatively coupled to the microfluidic heat exchange system 110. The heater control system 1005 includes at least one power supply 1015 communicatively coupled to a heater control unit 1020, which communicates with a control logic unit 1025. The heater control unit 1020 is adapted to control the power supply to the heaters, either on an individual basis or collectively to a group of heaters. This permits temporal and spatial control of heat supplied to the microfluidic heat exchange system 110.

The heater control system 1005 may include one or more temperature sensors 1010 positioned in or around the microfluidic heat exchange system 110 for sensing fluid temperature at one or more locations within the fluid flow path. The type of sensor can vary. In an embodiment, one or more thermocouples are used as the sensors 1010. The sensors 1010 communicate with the heater control unit 1020 and the control logic unit 1025 to provide a temperature feedback loop. The heater control system 1005 provides for feedback control of fluid temperature in the system to ensure, for example, that fluid is being heated to the required pasteurization temperature and/or that the fluid is not overheated or underheated. For example, the heater control unit 1020 in conjunction with the control logic unit 1025 may adjust power to one or more of the heaters based on a sensed temperature in order to achieve a desired temperature profile in one or more locations of the fluid flow path. The heater control system 1005 may include other types of sensors such as, for example, pressure sensors, flow rate sensors, etc. to monitor and adjust other parameters of the fluid as desired.

The heater control system 1005 may also be configured to provide one or more alarms, such as a visual and/or audio indication and/or a telecommunications signal, to the user or a remote monitor of system functions to inform such parties when the temperature is at an undesired level. For example, the control unit 1020 may comprise one or more temperature set limits within which to maintain, for example, the residence chamber temperature. If a limit is exceeded—i.e., if the temperature falls below the lower operating limit or above the upper operating limit, the control system may bypass the heater, set off an alarm and cease operation of the overall water purification system until the problem can be diagnosed and fixed by the operator. In this regard, the control system 1005 may include a reporting unit 1030 that includes a database. The reporting unit 1005 is configured to log and store data from the sensors and to communicate such data to a user or monitor of the system at a remote site.

Exemplary Fluid Purification Procedure

With reference again to FIG. 1, an exemplary configuration for purifying fluid using the fluid purification system is now described including a description of a fluid flow path through the system. It should be appreciated that the description is for example and that variations to the flow path as well as to the arrangement of the subsystems and hardware are possible. The fluid purification system is described in an exemplary context of being a component of a dialysis system. In this example, the fluid purification system is used to purify water that is used by the dialysis system. The fluid purification system is not limited to use for purifying water in dialysis systems.

As shown in FIG. 1, water enters the system via an entry location 105, flows along a flow pathway, and exits the system via an exit location 107. The flow pathway may be formed by any type of fluid conduit, such as piping. The piping may include one or more sample ports that provide access to water flowing through the piping. One or more subsystems, including the microfluidic heat exchange system 110, are positioned along the pathway for processing the water prior to the water exiting the system. As mentioned, the subsystems may include, for example, a sediment filter system 115, a carbon filter system 120, a reverse osmosis system 125, an ultrafilter system 130, an auxiliary heater system 135, a degassifier system 140, or any combination thereof.

The fluid purification system may also include hardware and/or software to achieve and control fluid flow through the fluid purification system. The hardware may include one or more pumps 150 and a throttling valve or other devices for driving fluid through the system, as well as sensors for sensing characteristics of the fluid and fluid flow, such as flow sensors, conductivity sensors, pressure sensors, etc. The hardware may communicate with a control system that controls operation of the hardware.

Upon entering the system, the water flows through at least one sediment filter system 115, which includes one or more sediment filters that filter sediment from the water flowing therethrough. The water then flows through a carbon filter system 120, which includes one or more carbon filters that filter organic chemicals, chlorine and chloramines in particular from the water. One or more pumps may be positioned at various locations along the water flow pathway such as between the filter subsystems. In addition, a conductivity sensor may be coupled to the pathway downstream of the carbon filter system 120 and downstream of the reverse osmosis system to determine the percentage of dissolves solids removed. The water flows from the carbon filter system 120 to a reverse osmosis system 125 configured to remove particles from the water pursuant a reverse osmosis procedure. The sediment filter 115 removes particulate matter down to 5 microns or even 1 micron. The carbon filter 120 removes chlorine compounds. The reverse osmosis system 125 usually removes greater than 95% of the total dissolved solids from the water.

The sediment filter system 115, carbon filter system 120, and reverse osmosis system 125 collectively form a pre-processing stage that removes a majority of dissolved solids, bacteria contamination, and chemical contamination, if any, from the water. The water is therefore in a somewhat macro-purified state prior to reaching the heat exchange system 110. Thus, the preprocessing stage supplies relatively clean water to the downstream pumps and also to the heat exchange system 110. This reduces or eliminates the potential for scale build-up and corrosion during heating of the water by the heat exchange system 110.

After the water passes the pre-processing stage, a pump 150 may be used to increase the water pressure to a level higher than the saturation pressure encountered in the heat exchange system 110. This would prevent phase change of the water inside the heat exchange system 110. Thus, if the highest temperature reached in the heat exchange system 110 is 150 degrees Celsius where the water would have a saturation pressure of 475 kPa (approximately 4.7 atmospheres or 69 psia), the pressure of the water coming out of the pump would exceed the saturation pressure. The pump desirably increases the water pressure to a level that is at or exceeds the saturation pressure to ensure no localized boiling. This can be important where the heat exchange system is used to pasteurize water and the water is exposed to high temperatures that may be greater than 138 degrees Celsius, i.e., well above the boiling point of water at atmospheric pressure.

The water, which is now pressurized above, or significantly above, the saturation pressure, enters the heat exchange system 110, which pasteurizes the water as described in detail above. The heat exchange system 110 may be encased in insulation to reduce the likelihood of heat loss of the water passing therethrough. After leaving the heat exchange system 110, the water passes into a throttling valve 160, which maintains the pressure though the water path from the pump 150 to outlet of the heat exchange system 110. The throttling valve 160 and the pump 150 may be controlled and adjusted to achieve a flow rate and a desired pressure configuration. The pump 150 and the throttling valve 160 may communicate with one another in a closed loop system to ensure the required pressure is maintained for the desired flow rate and temperature. A degassifier system 140 may also be incorporated into the flow path for removing entrained gas from the water.

After the water leaves the throttling valve 160, it passes to an ultrafilter system 130 that removes macromolecules and all or substantially all of the dead bacteria killed by the pasteurization process from the water to ensure no endotoxins remain in the water before mixing the dialysate. Where the water is used in a dialysis system, the presence of macromolecules may be detrimental to the dialysis process. The water then passes through a heater system that may heat the water to a desired temperature, such as to normal body temperature (98.6 degrees Fahrenheit). Where the water is used for dialysis, the water is then passed to a mixer 170 that mixes the clean water with a supply of concentrate solutions in order to make dialysate.

Startup and Shutdown of Fluid Purification System

Where the fluid purification system is used for dialysis, it is important to avoid bacterial contamination of the fluid flow path, both within the heat exchanger system 110 and throughout the components downstream of the heat exchanger system 110. In this regard, the heat exchanger system 110, which serves as a pasteurizer, is desirably operated in a manner that ensures clean fluid flow upon startup of the fluid purification system and also avoids bacterial contamination of the downstream components, or at least mitigates the contamination effects, upon shut down (i.e., when the heaters 220 are de-powered).

In an embodiment, clean fluid flow upon startup is achieved by initially flowing a sterilizing liquid through the heat exchanger system 110 while the heaters 220 are being powered up. The sterilizing liquid then flows through all the components downstream of the heat exchanger system 110 until the heat exchanger system 110 attains a desired operating temperature. Upon the heat exchanger system 110 reaching the desired operating temperature, fluid flow to the heat exchanger system 110 switches to water from the reverse osmosis system 125. The water passes through the heat exchanger system 110 (which has achieved the desired operating temperature) to flush the sterilizing liquid out of the flow pathway of the heat exchanger system 110. Various sterilizing solutions may be used. The solution, for example, can be a 1% chlorine in water mixture, or some other widely recognized water additive that can kill bacteria.

The fluid purification system may be shut down as follows. The heaters 220 are de-powered while fluid flow through the heat exchanger system 110 is maintained. Alternatively, a sterilizing liquid may be flowed through the heat exchanger system 110 until the heat exchanger system 110 attains near room temperature conditions. In this manner, the flow pathway is maintained in a sterilized condition as the heat exchanger system 110 shuts down. The flow pathway of the heat exchanger system 110 is then closed or "locked down" with sterilizing liquid present in the flow pathway of the heat exchanger system 110. The presence of the sterilizing liquid greatly reduces the likelihood of bacterial contamination during shutdown.

In another embodiment, one or more valves are positioned in the flow pathway of fluid purification system wherein the valves allow a circulating flow of solution to loop through the pump 150, heat exchanger system 110, and downstream components in a recirculation loop until desired pasteurization conditions are achieved during startup. The valves are then set to allow the sterilizing liquid to be flushed from the system. An auxiliary component, such as a microchannel fluid heater (without heat exchange capability), can also be incorporated to provide the ability to circulated a warmed (e.g., less than 100 degrees Celsius) sterilizing liquid through the downstream components and/or through the unpowered heat exchanger system 110. The sterilizing liquid can be used during either a start-up or shut-down process for keeping the flow pathway and components clean over the span of weeks and/or months. The use of a recirculation loop for sterilizing liquid at start up is another manner to prevent bacteria from entering the fluid purification system before the heat exchanger system 110 achieves operating temperatures. A timing control logic may be used with a temperature sensing capability to implement a process that ensures quality control over the start-up and shut down processes. The control logic may be configured to initiate flow only after the heat exchanger system 110 or a heater attains a preset temperature.

The flow path may include one or more bypass circulation routes that permit circulation of cleaning and/or sterilization fluid through the flow path. The circulation route may be an open flow loop wherein fluid flowing through the circulation route is dischargeable from the system after use. In another embodiment, the circulation route may be a closed flow loop wherein fluid flowing the circulation route not dischargeable from the system. Alternately, the system may include both open and closed circulation routes.

The present specification is related to subject matter disclosed in U.S. Pat. No. 8,753,515 entitled "Dialysis System with Ultrafiltration Control," filed on Jun. 7, 2010, naming James R. Curtis, Ladislaus F. Nonn, and Julie Wrazel, and U.S. Pat. No. 8,801,922, entitled "Dialysis System," filed on Jun. 7, 2010, naming Julie Wrazel, James R. Curtis, Ladislaus F. Nonn, Richard B. Peterson, Hailei Wang, Robbie Ingram-Goble, Luke W. Fisher, Anna B. Garrision, M. Kevin Drost, Goran Jovanovic, Richard Todd Miller, Bruce Johnson, Alana Warner-Tuhy and Eric K. Anderson, which are incorporated herein by reference in their entirety.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

We claim:

1. A fluid purification system comprising:
a pump adapted to pump household water through a pump outlet;
a microfluidic heat exchanger downstream of the pump and coupled to the fluid
flow pathway, the microfluidic heat exchanger comprising an inlet in fluid
communication with the pump outlet, an inflow microchannel downstream of the inlet, a heater downstream of the inflow microchannel, an outflow microchannel downstream of the heater and in thermal communication with the inflow microchannel to permit heat transfer between water flowing in the outflow microchannel and water flowing in the inflow microchannel, the microfluidic heat exchanger being configured to heat the water to a pasteurization temperature, maintain the water at the pasteurization temperature for a period of time effective to pasteurize the water, and cool the pasteurized water to a temperature lower than the pasteurization temperature; and
a mixer downstream of the microfluidic heat exchanger, the mixer comprising dialysate components for addition to water flowing from the microfluidic heat exchanger.

2. The system of claim 1 wherein the microfluidic heat exchanger further comprises a plurality of inflow microchannels in fluid communication with the inlet and a plurality of outflow microchannels in fluid communication with the mixer.

3. The system of claim 2 wherein the microchannels are disposed in a plurality of stacked laminae.

4. The system of claim 3 wherein the inflow microchannels and the outflow microchannels are separated by the laminae.

5. The system of claim 4 wherein the inflow microchannels and the outflow microchannels are formed from flow paths etched in facing surfaces of adjacent laminae.

6. The system of claim 3 wherein the microfluidic heat exchanger further comprises a heat transfer layer disposed between a lamina of inflow microchannels and a lamina of outflow microchannels.

7. The system of claim 3 wherein the inlet comprises an inlet opening extending through a plurality of laminae in fluid communication with the plurality of inflow microchannels in the plurality of laminae.

8. The system of claim 3 wherein the microfluidic heat exchanger further comprises an outlet opening extending through a plurality of laminae and in fluid communication with the plurality of outflow microchannels in the plurality of laminae and with the mixer.

9. The system of claim 3 wherein the microfluidic heat exchanger further comprises a heater region in which the heater is disposed, the heater region being in fluid communication with a plurality of laminae.

10. The system of claim 2 wherein the microfluidic heat exchanger further comprises a residence chamber comprising a flow pathway downstream of the heater and upstream of the outflow microchannels.

11. The system of claim 1 wherein the inlet microchannel and the outlet microchannel are disposed in a counterflow arrangement.

* * * * *